US010188289B2

(12) United States Patent
Gill et al.

(10) Patent No.: US 10,188,289 B2
(45) Date of Patent: Jan. 29, 2019

(54) SYSTEMS AND METHODS FOR LENSED AND LENSLESS OPTICAL SENSING

(71) Applicant: Rambus Inc., Sunnyvale, CA (US)

(72) Inventors: Patrick R. Gill, Sunnyvale, CA (US); David G. Stork, Portola Valley, CA (US)

(73) Assignee: Rambus Inc., Sunnyvale, CA (US)

(*) Notice: Subject to any disclaimer, the term of this patent is extended or adjusted under 35 U.S.C. 154(b) by 0 days.

(21) Appl. No.: 15/314,404

(22) PCT Filed: Jun. 9, 2015

(86) PCT No.: PCT/US2015/034966
§ 371 (c)(1),
(2) Date: Nov. 28, 2016

(87) PCT Pub. No.: WO2015/195417
PCT Pub. Date: Dec. 23, 2015

(65) Prior Publication Data
US 2017/0112376 A1   Apr. 27, 2017

Related U.S. Application Data

(60) Provisional application No. 62/015,369, filed on Jun. 20, 2014.

(51) Int. Cl.
*A61B 3/14* (2006.01)
*A61B 3/02* (2006.01)
(Continued)

(52) U.S. Cl.
CPC .............. *A61B 3/113* (2013.01); *A61B 3/14* (2013.01); *A61B 3/145* (2013.01); *A61B 3/152* (2013.01);
(Continued)

(58) Field of Classification Search
CPC ......... A61B 3/113; A61B 3/0025; A61B 3/14; G06K 9/00604; G06K 9/0061
(Continued)

(56) References Cited

U.S. PATENT DOCUMENTS 4,720,189 A   1/1988   Heynen et al.
5,536,924 A   7/1996   Ackley
(Continued)

FOREIGN PATENT DOCUMENTS

WO   WO-99/35523   7/1999

OTHER PUBLICATIONS

Garcia-Martinez et al., "Generation of Bessel Beam Arrays Through Dammann Gratings", Mar. 20, 2012, vol. 51, No. 9, Applied Optics. pp. 1375-1381. 7 Pages.
(Continued)

*Primary Examiner* — Mohammed Hasan
(74) *Attorney, Agent, or Firm* — Silicon Edge Law Group LLP; Arthur J. Behiel

(57) ABSTRACT

A sensing device with an odd-symmetry grating projects near-field spatial modulations onto an array of closely spaced pixels. Due to physical properties of the grating, the spatial modulations are in focus for a range of wavelengths and spacings. The spatial modulations are captured by the array, and photographs and other image information can be extracted from the resultant data. Pixels responsive to infrared light can be used to make thermal imaging devices and other types of thermal sensors. Some sensors are well adapted for tracking eye movements, and others for imaging barcodes and like binary images. In the latter case, the known binary property of the expected images can be used to simplify the process of extracting image data.

19 Claims, 28 Drawing Sheets

(51) Int. Cl.
*A61B 3/113* (2006.01)
*G02B 5/18* (2006.01)
*G02B 27/42* (2006.01)
*G06T 3/40* (2006.01)
*H04N 5/33* (2006.01)
*G06K 9/00* (2006.01)
*H04N 5/225* (2006.01)
*H04N 7/18* (2006.01)
*A61B 3/15* (2006.01)
*H04N 5/213* (2006.01)
*H04N 5/232* (2006.01)
*H04N 9/04* (2006.01)
*H04N 9/097* (2006.01)

(52) U.S. Cl.
CPC ......... *G02B 5/1871* (2013.01); *G02B 5/1876* (2013.01); *G02B 27/4205* (2013.01); *G06K 9/00604* (2013.01); *G06T 3/4053* (2013.01); *H04N 5/2253* (2013.01); *H04N 5/2256* (2013.01); *H04N 5/33* (2013.01); *H04N 5/332* (2013.01); *H04N 7/181* (2013.01); *H04N 5/213* (2013.01); *H04N 5/23241* (2013.01); *H04N 5/23245* (2013.01); *H04N 9/045* (2013.01); *H04N 9/097* (2013.01); *H04N 2209/048* (2013.01)

(58) Field of Classification Search
USPC .................................................. 351/200–246
See application file for complete search history.

(56) References Cited

U.S. PATENT DOCUMENTS

| 5,703,637 | A | 12/1997 | Miyazaki et al. |
| 6,344,893 | B1 | 2/2002 | Mendlovic et al. |
| 2003/0103150 | A1 | 6/2003 | Catrysse et al. |
| 2008/0170225 | A1 | 7/2008 | deBoer et al. |
| 2010/0202725 | A1 | 8/2010 | Popovich et al. |
| 2011/0109880 | A1* | 5/2011 | Nummela ............ A61B 3/113 351/210 |
| 2011/0248151 | A1 | 10/2011 | Holcombe et al. |
| 2013/0077049 | A1 | 3/2013 | Bohn |
| 2014/0253781 | A1 | 9/2014 | Gill et al. |
| 2016/0169667 | A1* | 6/2016 | Stork ............... G01B 11/26 356/496 |

OTHER PUBLICATIONS

Gill, Patrick et al., "Lensless Ultra-Miniature Imagers Using Odd-Symmetry Spiral Phase Gratings", article presented at Computational Optical Sensing and Imaging (COSI), Arlington, Virginia, Jun. 23-27, 2013. 3 pages.

Gill, Patrick et al., "Lensless Ultra-Miniature Imagers Using Odd-Symmetry Spiral Phase Gratings", slide deck presented at Computational Optical Sensing and Imaging (COSI), Arlington, Virginia, Jun. 23-27, 2013. 18 pages.

Guerineau et al., "Generation of Achromatic and Propagation-Invariant Spot Arrays by Use of Continuously Self-Imaging Gratings," Apr. 1, 2001, vol. 26, No. 7, Optics Letters. pp. 411-413. 3 Pages.

ISR—Notification of Transmittal of the International Search Report and the Written Opinion of the International Searching Authority dated Oct. 16, 2015 re Intl. Appln. No. PCT/US2015/034966. 11 Pages.

Morrison, Rick L., "Symmetries that simplify the design of spot array phase gratings", Journal of the Optical Society of America A, vol. 9, Issue 3, pp. 464-471, 1992. 8 pages.

Notification Concerning Transmittal of International Preliminary Report on Patentability dated Dec. 29, 2016 re: International Appl. No. PCT/US15/034966. 7 Pages.

Stork, David et al, "Lensless Ultra-Minature CMOS Computational Imagers and Sensors" SensorComm 2013, Barcelona, Spain, Aug. 26, 2013. 59 Pages.

Extended European Search Report dated Jan. 30, 2018 re: EP Appln. No. 15809767.5. 11 Pages.

Applicant's Jul. 24, 2018 response to the Extended European Search Report dated Jan. 30, 2018 re: EP Appln. No. 15809767.5. 13 Pages.

* cited by examiner

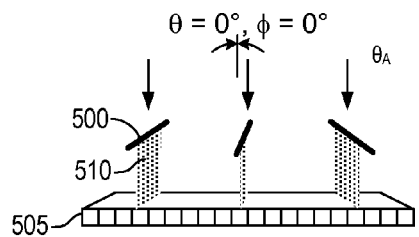
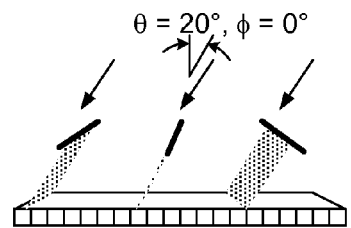
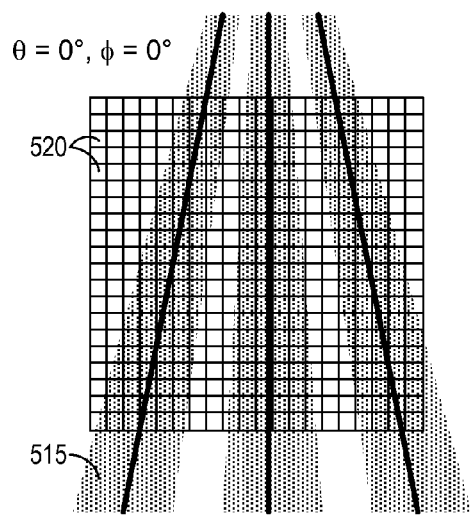
FIG. 5A     FIG. 5B
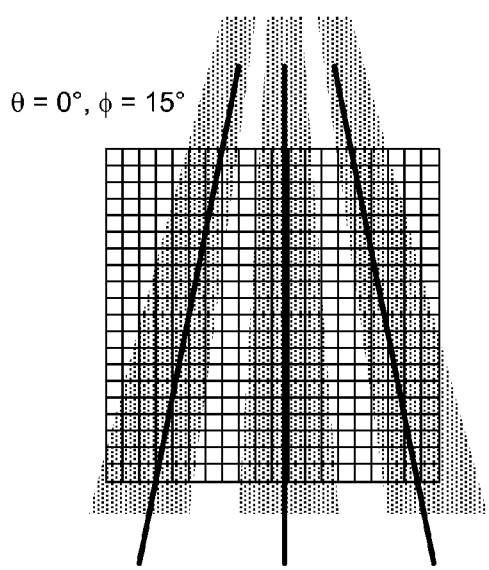
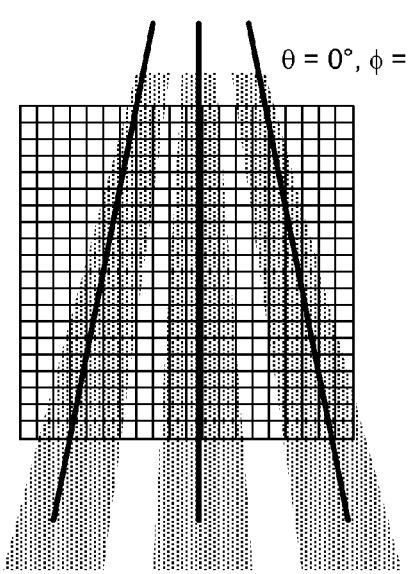
FIG. 5C     FIG. 5D

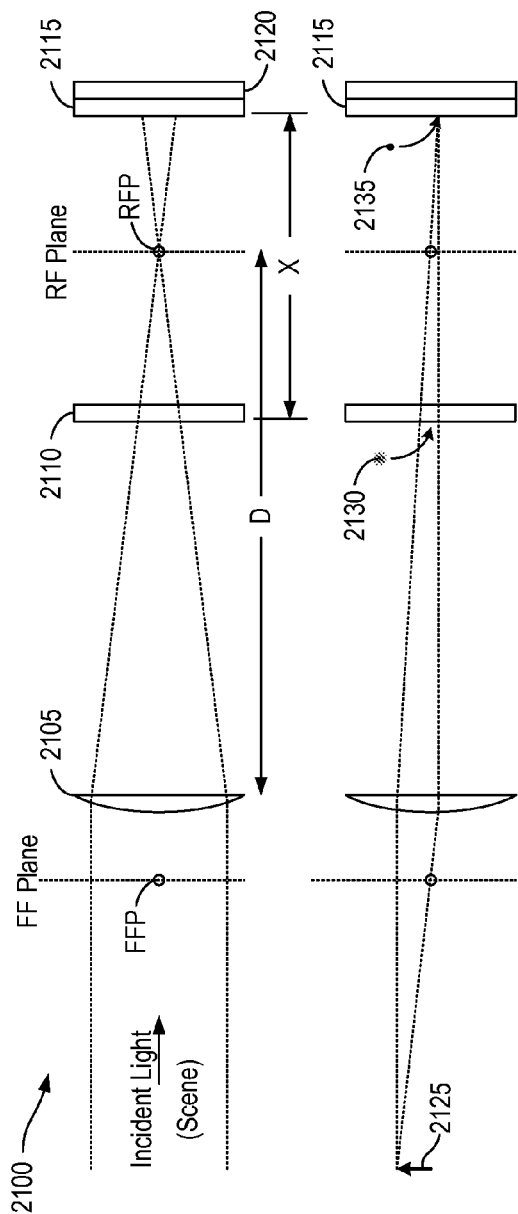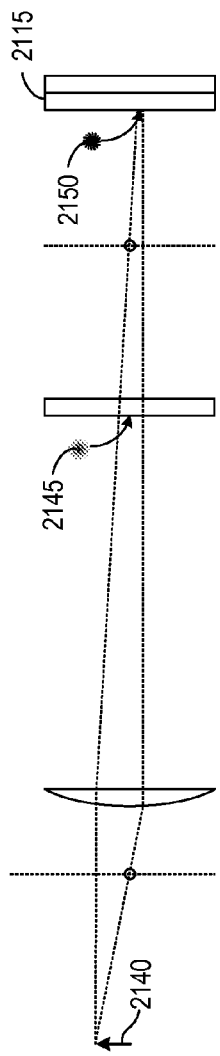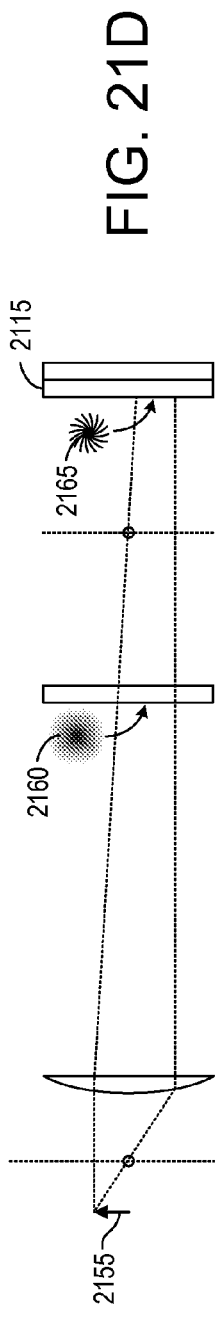
FIG. 21A
FIG. 21B
FIG. 21C
FIG. 21D

2700

2705

2800

2900

SYSTEMS AND METHODS FOR LENSED AND LENSLESS OPTICAL SENSING

BACKGROUND

Traditional cameras use a lens or lenses to image each point in a scene onto a single point on a sensor. In digital cameras, the sensor is a two-dimensional array of picture elements, or "pixels," that encodes the imaged scene into digital image data for storage, processing, and reproduction.

Digital imaging has enabled new imaging architectures. Cathey and Dowski took an early and conceptually important step away from the traditional model by exploiting digital processing. They designed a cubic-phase optical plate which, when inserted into the optical path of a traditional camera, led to an image whose (significant) blur was independent of the object depth: the image on the sensor plane did not "look good" as it would in a traditional camera. However, subsequent image processing sharpened the entire blurred image, thus leading to enhanced depth of field. Since then the field of computational imaging has explored imaging architectures in which the raw signals do not superficially resemble a traditional image; instead, the final image is computed from such signals. More and more of the total imaging "burden" is borne by computation, thereby expanding the class of usable optical components. In this way, many optical aberrations can be corrected computationally rather than optically. This imaging paradigm has led to new conceptual foundations of joint design of optics and image processing, as well as a wide range of non-standard imaging architectures such as plenoptic, coded-aperture and multi-aperture systems, each with associated methods of signal processing.

The economic pressures for miniaturization of electronic devices, including cameras, arising in the mobile computing market have led to smaller imager form factors. Recently, a new miniature imaging architecture has been explored, one based on integrating diffractive optics with photodetector arrays. This architecture forgoes lenses and relies instead on diffraction gratings that can be created using processes similar to those used to create the underlying sensor. For a given image resolution, such diffractive elements enable the construction of imaging devices much smaller than possible using the optical paths of traditional cameras, and at a much lower cost.

BRIEF DESCRIPTION OF THE DRAWINGS

The detailed description is illustrated by way of example, and not by way of limitation, in the figures of the accompanying drawings and in which like reference numerals refer to similar elements and in which:

FIGS. 5A, 5B, 5C, and 5D each depict three boundaries of odd symmetry 500 over a two-dimensional photodiode array 505.

FIG. 21A depicts a camera 2100 in accordance with an embodiment that includes a lens 2105.

FIG. 21B is an example of camera 2100 with a point source 2125 imaged in focus on array 2115.

FIG. 21C is an example of camera 2100 with a point source 2140 imaged out of focus on array 2115.

FIG. 21D is an example of camera 2100 with a point source 2155 imaged more out of focus than point source 2140 in the example of FIG. 21C.

DETAILED DESCRIPTION

Figure 1A:
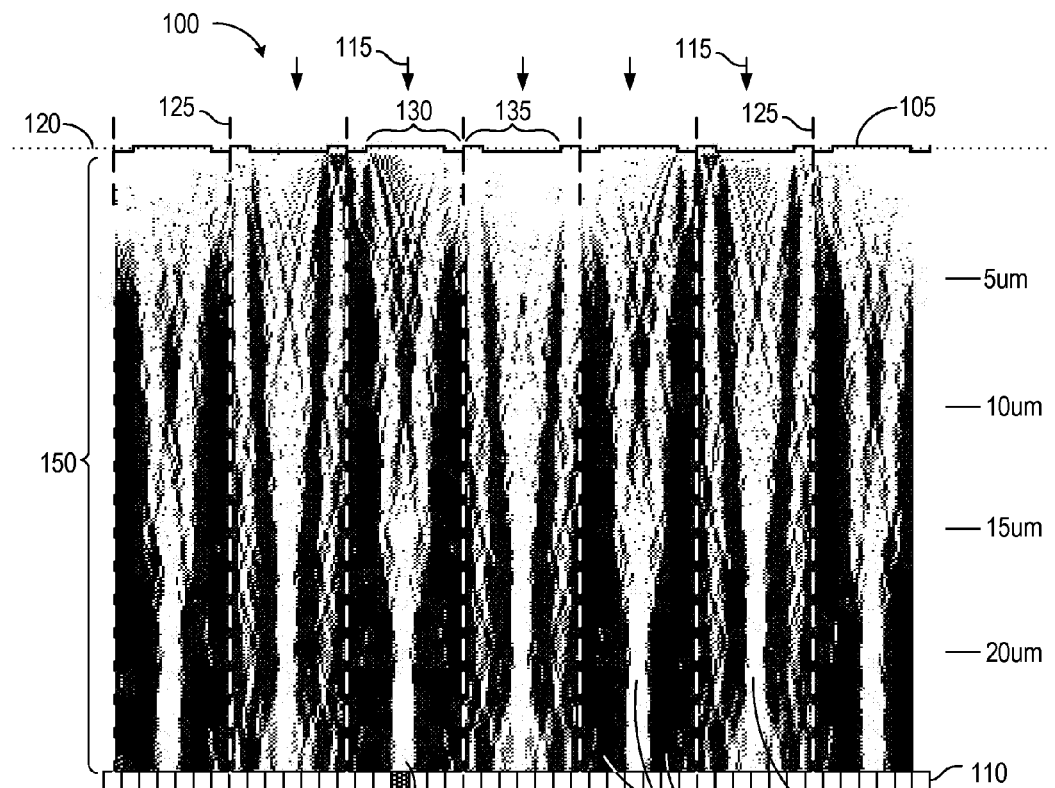
FIG. 1A is a cut-away view of a sensing device 100 with an odd-symmetry grating 105 overlying a photodetector array 110, such as a CCD (charge-coupled device) or CMOS (complementary metal-oxide-semiconductor) sensor.

FIG. 1A is a cut-away view of a sensing device 100 with an odd-symmetry grating 105 overlying a photodetector array 110, such as a CCD (charge-coupled device) or CMOS (complementary metal-oxide-semiconductor) sensor. The features of grating 105 offer considerable insensitivity to the wavelength of incident light in a wavelength band of interest, and also to the manufactured distance between grating 105 and photodetector array 110. Grating 105 produces an interference pattern for capture by array 110. Photographs and other image information can then be extracted from the pattern.

Light in a wavelength band of interest—such as the visible spectrum—is incident grating 105 from a direction 115 that is normal to a transverse plane 120 of the grating 105. Dashed lines 125 highlight periodic boundaries of substantially odd symmetry. Each of these boundaries is a result of features 130 and 135 of odd symmetry, and produces a normally arranged curtain 140 of minimum intensity created by destructive phase interference between adjacent features 130 and 135. Curtains 140 are separated by foci 145, and the collection of curtains 140 and foci 145 (curtains of maximum light intensity) extend from grating 105 through the body 150 of device 100 to produce an interference pattern on photodetector array 110. In this illustration, the pattern of intensity variations evident in the foci and curtains are near-field spatial modulations that result from near-field diffraction. One photosensitive element 155 within array 110 is shaded beneath a focus 145 to serve as a reference for a subsequent discussion of the sensitivity of device 100 to the angle of incident light; however, other photosensitive elements 155 beneath corresponding foci likewise respond to incident light.

The image of FIG. 1A resulted from a simulation of a sensing device with the following parameters and assuming specific parameters. Body 150 is of fused silica, and is in contact with a conventional photodetector array 110 with photosensitive elements spaced by 2.2 um. The top of grating 105 is an air interface in this example. The relatively small segments of features 130 and 135 are about 1 um, and the relatively larger segments are about 4 um. These segments generally form transverse plane 120, which is separate from array 110 by about 25 um. Curtains 140 and foci 145 are the destructive and constructive interference patterns for 532 nm incident light. Responsive to a point source, grating 105 thus induces near-field spatial modulations that illuminate a pattern over nonadjacent pixels.

The thickness of body 150 and lengths of the segments of features 130 and 135 were optimized for 400 nm light despite the selection of 532 nm light for the simulation. As a consequence, the tightest focus occurs about 5um above array 110 (at the 20 um mark). The resultant curtains 140 plainly separate foci 145 well above and below the 20 um mark, however, illustrating a robust insensitivity to wavelength within the band of interest. The relatively deep and continuous penetration of curtains 140 also provides considerable manufacturing tolerance for the thickness of body 150. These advantages obtain because the near-field spatial modulations projected onto array 110 are wavelength independent over the wavelength band of interest, which means that the adjacent modulations (dark and light) do not reverse signs with changes in wavelength within the band of interest.

Figure 1B:
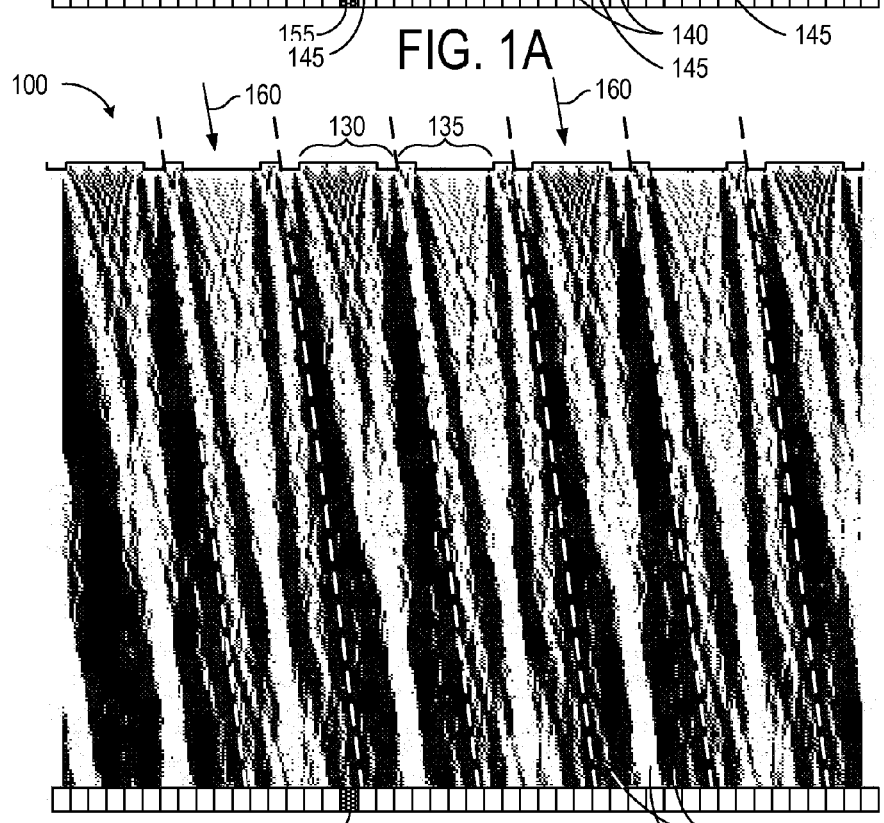
FIG. 1B depicts sensor 100 of FIG. 1A simulating light incident plane 120 at an acute angle 160 to illustrate the sensitivity of curtains 140 and foci 145 to the angle of incidence.

FIG. 1B depicts sensor 100 of FIG. 1A simulating light incident plane 120 at an acute angle 160 to illustrate the sensitivity of curtains 140 and foci 145 to the angle of incidence. Using element 155 as a reference point, we see that the foci 145 that illuminated element 155 in FIG. 1A has considerably moved to the right in FIG. 1B. Curtains 140 and foci 145 extend at an acute angle that relates to angle 160 according to Snell's law. The separation of foci 145 by curtains 140 is maintained. Sensor 100 is thus sensitive to the angle of incidence.

Figure 2:
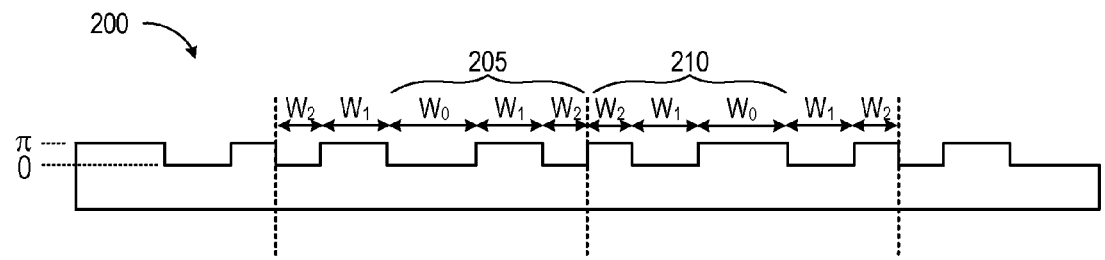
FIG. 2 depicts a binary odd-symmetry grating 200 in accordance with one embodiment.

FIG. 2 depicts a binary odd-symmetry grating 200 in accordance with one embodiment. Each of three boundaries of odd symmetry is indicated using a vertical, dashed line. The upper features of grating 200 are at a height sufficient to induce one half wavelength of retardation in the band of interest relative to lower features, or $\pi$ radians of relative phase delay. Features 205 and 210 on either side of each boundary exhibit odd symmetry with three differently sized segments $W_0$, $W_1$, and $W_2$. With this arrangement, paired segments (e.g., $W_0$ within features 205 and 210) induce respective phase delays that differ by approximately half a wavelength over the wavelength band of interest.

Figure 3:
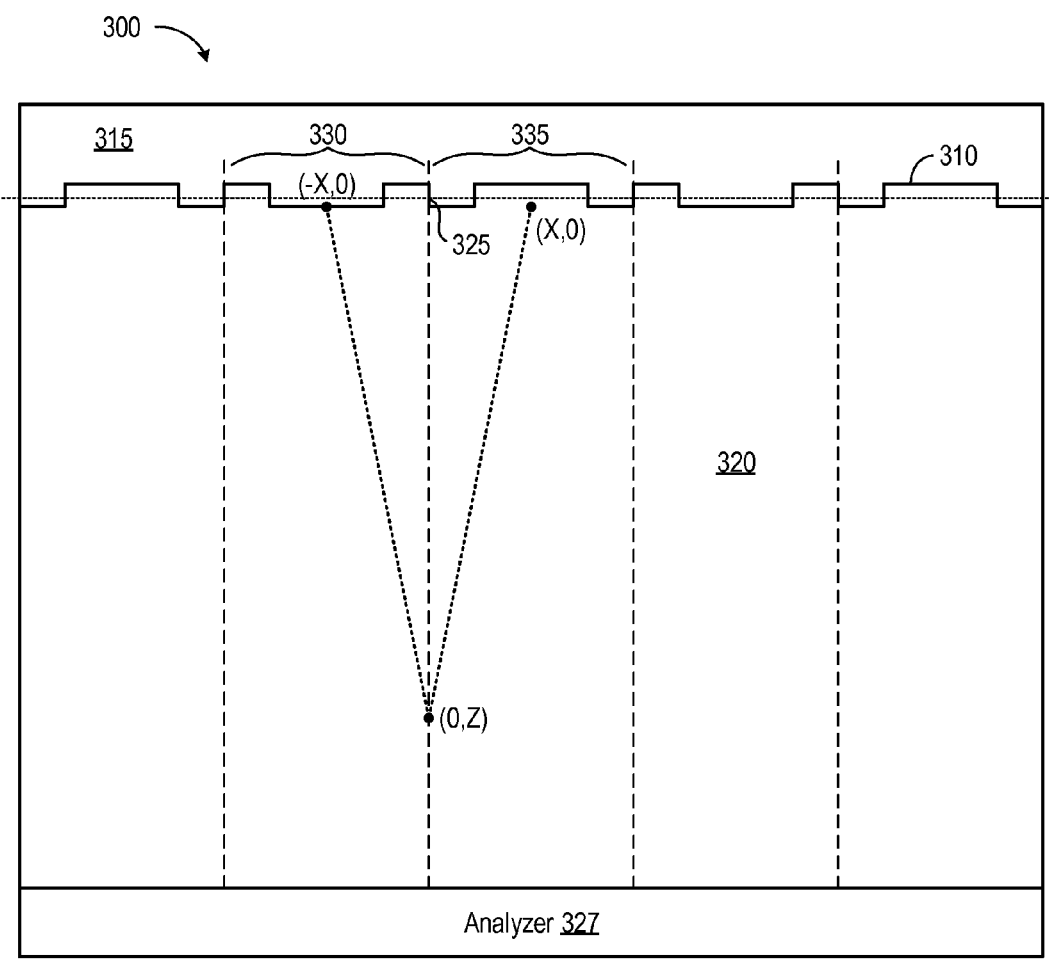
FIG. 3 depicts a sensing device 300 in accordance with an embodiment in which a binary, odd-symmetry phase grating 310 is formed by an interface between materials of two different refractive indices.

FIG. 3 depicts a sensing device 300 in accordance with an embodiment in which a binary, odd-symmetry phase grating 310 is formed by an interface between materials of two different refractive indices, a polycarbonate layer 315 and optical lanthanum dense flint glass 320 in this example. Each of four boundaries of odd symmetry 325 is indicated using a vertical, dashed line. As in the foregoing examples, the upper features of grating 310 induce phase retardations of half of one wavelength ($\pi$ radians) relative to lower features. Features 330 and 335 on either side of each boundary exhibit odd symmetry. With this arrangement, paired features induce respective phase delays that differ by approximately half a wavelength over the wavelength band of interest.

These elements produce an interference pattern on an analyzer layer 327 (e.g., a conventional photodiode array) in the manner detailed in connection with FIGS. 1A and 1B. This example assumes light incident the light interface of grating 300 is normal to the transverse plane of phase grating 310, in which case light fields that enter grating 310 equidistant from one of the boundaries of odd symmetry 325, such as at locations (−X,0) and (X,0), are out of phase at points beneath array 310 (e.g., point (0,Z)), and thus destructively interfere to produce curtains of minimum intensity (e.g., curtains 140 of FIG. 1). Neither the depth Z nor the wavelength of light over a substantial spectrum significantly influences this destructive interference. Constructive interference similarly produces foci of maximum intensity (e.g., foci 145 of FIG. 1). Both the high and low features admit light, which provides relatively high quantum efficiency relative to gratings that selectively block light.

The following discussion details phase gratings in accordance with examples described by Patrick R. Gill and David G. Stork in an upcoming paper. "Lensless Ultra-Miniature Imagers Using Odd-Symmetry Spiral Phase Gratings." © 2013 *Optical Society of America*. In that article, Gill and Stork describe a phase grating formed by a high-n, low-dispersion substrate and a low-n, high-dispersion coating that can introduce approximately $\lambda$-independent phase shifts in all normally incident visible light. Similar gratings are discussed above. If there exist certain points p on this interface that satisfy the following symmetry in their transmission t(•) and phase retardation φ(•), $$t(p+y)=t(p-y) \forall y \quad (1)$$

$$\phi(p+y)=\phi(p-y)+\pi+2n\pi \forall y, n \in I \quad (2)$$

where y is a horizontal translation transverse to the grating direction, then the grating has odd symmetry about points p, and light will interfere destructively below p, regardless of $\lambda$ and depth z.

A linear odd-symmetry grating above a photosensor array could pass information from a single spatial orientation of features in the far field (transverse to the grating orientation). However, to capture information about arbitrarily oriented features of a complex scene, it is preferable to have a complete distribution of orientations in the diffractive optic. More generally, if the point-source responses (PSRs) are approximately spatially invariant, the transfer function of the imager approximates convolution with the PSR function. In such a case, the PSR should have significant power at all 2D spatial frequencies to make the inversion problem of image recovery well-conditioned.

In one example provided in Gill and Stork, gratings were numerically optimized to focus visible light onto a photodetector array 100 µm below. Optical simulations estimated the imaging performance of such a device from a 60×60 pixel array with 2.2 µm pitch 100 µm below the gratings with the sensor illuminated by a complex scene far ($\gg$ 100 µm) from the sensor. The resultant photocurrent from the pixel array was unintelligible; however, the scene was reconstructed to a higher resolution than possible using a much larger diffractive imagers based on Talbot-effect angle-sensitive using Tikhonov regularization. Gill and Stork report that compressed sensing techniques could be applied to improve the reconstruction quality if the scene is known to have a compressible structure. Compressed sensing could be especially advantageous if small gaps in the Fourier transform of the PSR exist.

Figure 4A:
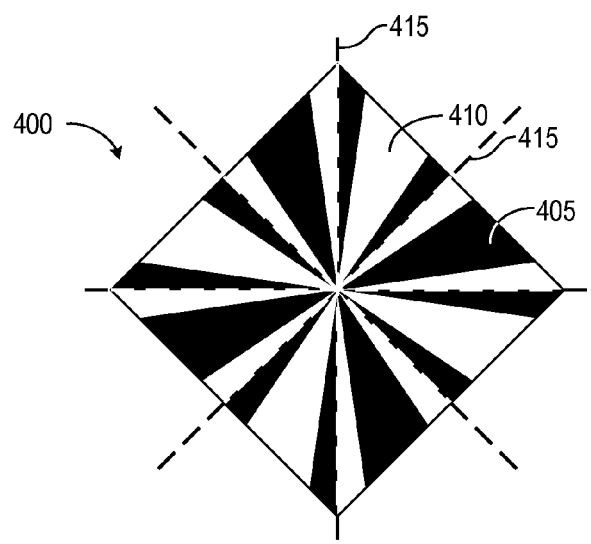
FIG. 4A is a plan view of a sensor 400 in accordance with another embodiment.

FIG. 4A is a plan view of a sensor 400 in accordance with another embodiment. Relatively high segments 405 and low segments 410 on either side of each of eight boundaries of odd symmetry 415 create a grating in which the widths of the segments increase with distance from the center of the sensor. For a given focal depth, light of higher frequencies tends to produce a sharper focus with narrower feature widths. Sensor 400 can therefore be optimized such that the central portion of the grating is optimized for collection of relatively higher frequency light, and the peripheral area for collection of relatively lower frequency light. This topic is detailed below in connection with other Figures.

Figure 4B:
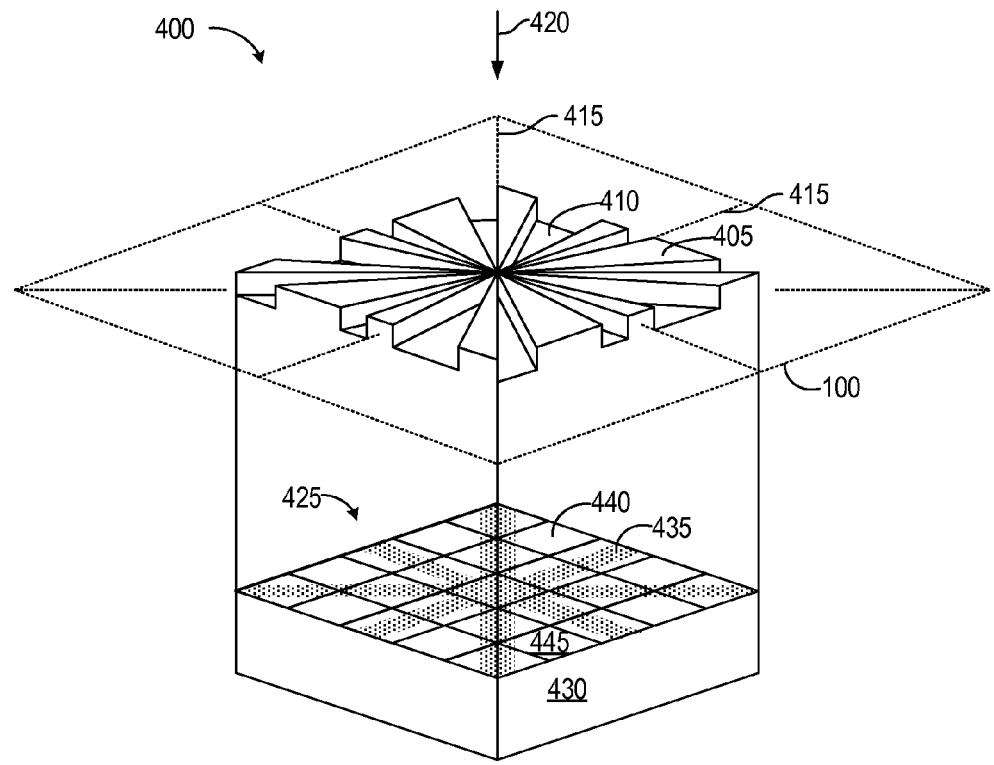
FIG. 4B is a three-dimensional perspective of sensor 400 of FIG. 4A, and shows how light 420 from a direction normal to the grating surface casts an interference pattern 425 on an underlying photodiode array 430.

FIG. 4B is a three-dimensional perspective of sensor 400 of FIG. 4A, and shows how light 420 from a direction normal to the grating surface casts an interference pattern 425 on an underlying photodiode array 430. Curtains and foci, as detailed previously, respectively cast shadows 435 and bright shapes 440 to be sensed by individual photosensitive elements 445 of array 430. Array 430 captures a digital representation of pattern 425.

FIGS. 5A, 5B, 5C, and 5D each depict three boundaries of odd symmetry 500 over a two-dimensional photodiode array 505. Curtains 510 cast shadows 515 on the underlying photodetectors 520, and the patterns thus created are different depending upon the angle of incident light. Array 505 can therefore sample the resultant interference pattern to obtain information as to the angle of incidence.

Figure 6:
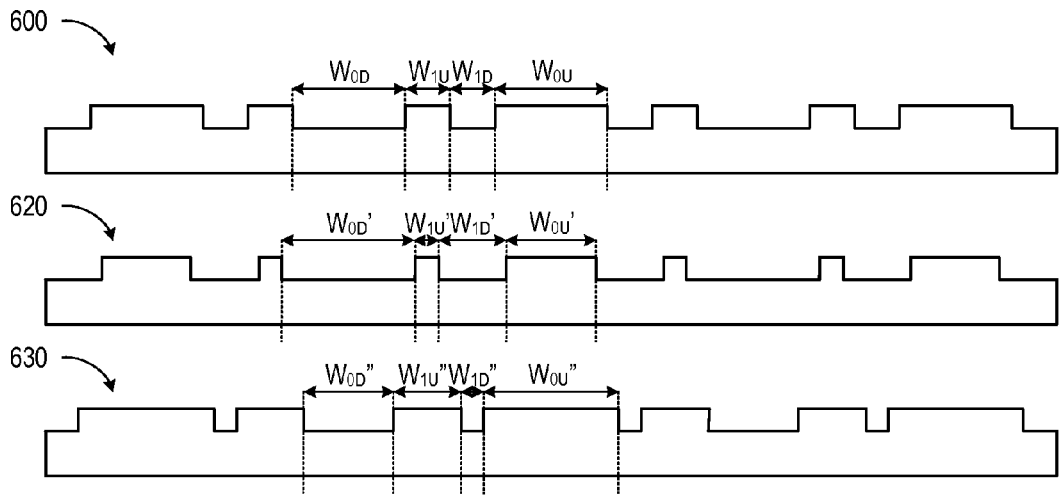
FIG. 6 depicts three odd-symmetry gratings 600, 620, and 630, each with feature segments of different relative widths.

FIG. 6 depicts three odd-symmetry gratings 600, 620, and 630, each with feature segments of different relative widths. It can be useful to create a sensor with multiple width ratios, as shown, to compensate for manufacturing tolerances that impact the relative heights of the grating features. Assuming, for example, that grating 600 is width optimized for a manufacturing process of interest, but that the process produces a relative phase delay of 40% rather than the ideal 50% to form curtains of minimum intensity at the desired positions. To a first order the increased width of the relatively wide segments, as depicted in grating 630, can improve the distortion resulting from the erroneous phase offset. Phase offsets above 50% can be corrected for by narrowing the relatively wide segments, as depicted in grating 620. Some embodiments include a mixture of relative segment widths covering different areas of a photodiode array to accommodate manufacturing tolerances. Images associated with the gratings that provide the sharpest focus, or the sharpest focus for a wavelength or range of wavelengths, can be selected or combined to obtain the desired image data. The different gratings may also perform better for light of different wavelengths or incident angles, so selection of which gratings to use for a given image may be optimized for variables other than manufacturing tolerances.

Figure 7A:
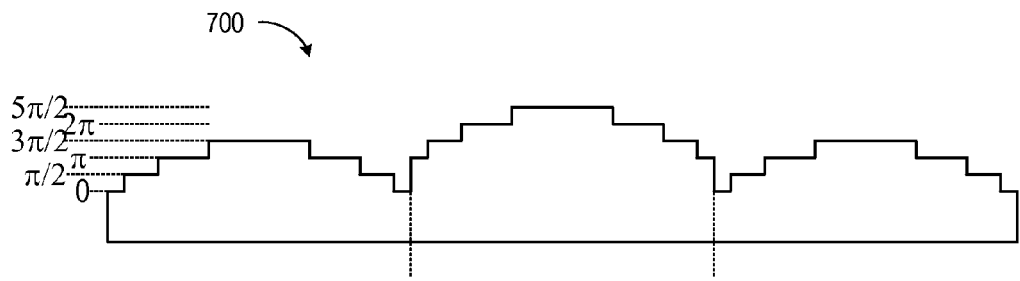
FIG. 7A is a cross-section of a phase grating 700 in accordance with an embodiment that uses more than two levels to produce an odd symmetry.

FIG. 7A is a cross-section of a phase grating 700 in accordance with an embodiment that uses more than two levels to produce an odd symmetry. Additional levels may allow for sharper focus, but may require more complex manufacturing processes. If gratings are to be made using photolithography, for example, additional levels require additional mask steps. Paired surfaces on either side of each boundary of odd symmetry introduce respective paired phase delays that differ by approximately half a wavelength, plus an integer number of wavelengths, over the wavelength band of interest.

Figure 7B:
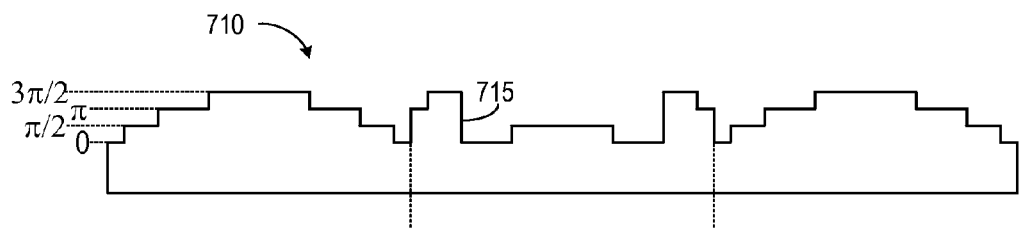
FIG. 7B is a cross-section of a phase grating 710 that is optically similar to phase grating 700 of FIG. 7A, but uses fewer layers.

FIG. 7B is a cross-section of a phase grating 710 that is optically similar to phase grating 700 of FIG. 7A, but uses fewer layers. The resultant larger abrupt discontinuities 715 may introduce undesirable image artifacts or may be difficult to manufacture accurately, but the reduced number of levels may reduce manufacturing costs.

Figure 8:
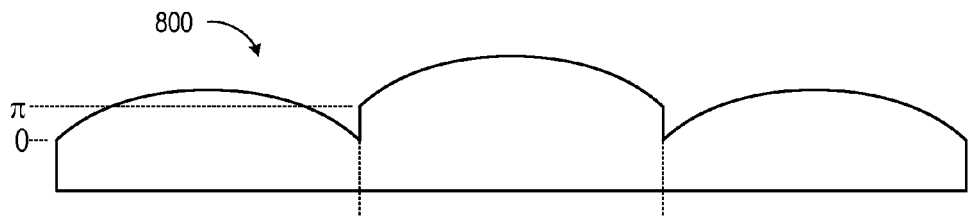
FIG. 8 is a cross-section of a phase grating 800 that illustrates how odd symmetry can be extended to curved functions.

FIG. 8 is a cross-section of a phase grating 800 that illustrates how odd symmetry can be extended to curved functions.

Figure 9:
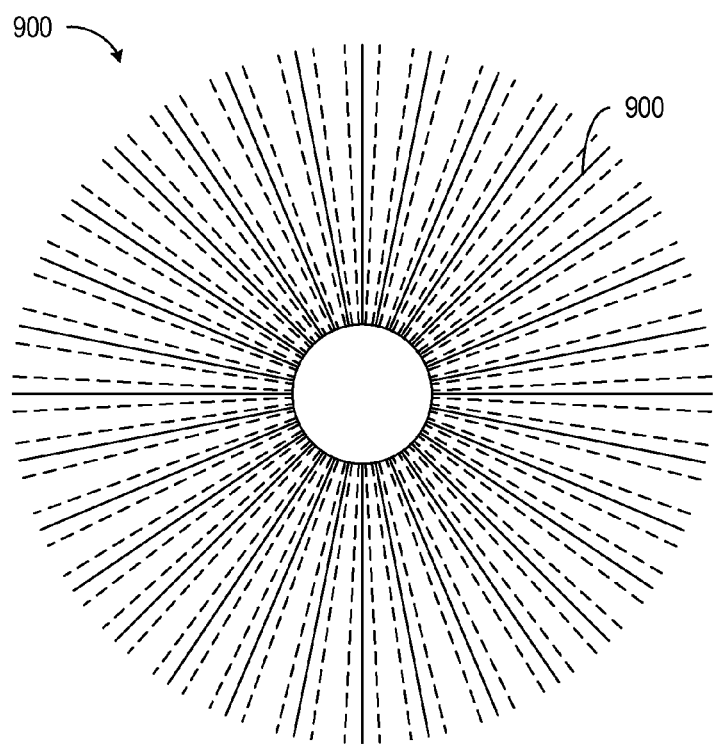
FIG. 9 is a plan view of a grating 900 in accordance with an embodiment in which boundaries of odd symmetry 905 extend radially from the center of the grating, and in which the widths of the feature segments widen gradually away from the center.

FIG. 9 is a plan view of a grating 900 in accordance with an embodiment in which boundaries of odd symmetry 905 extend radially from the center of the grating, and in which the widths of the feature segments widen gradually away from the center. Grating 900 captures image information at sixteen discrete angles with a continuously variable set of widths. While convenient to draw grating 900 as a circle, other shapes may be used. In some embodiments, for example, collections of gratings are arrayed over a photodiode array. In such cases grids that share common boundaries (e.g., such as hexagonal, square, or triangular boundaries) make more efficient use of the underlying photodiodes.

Figure 10:
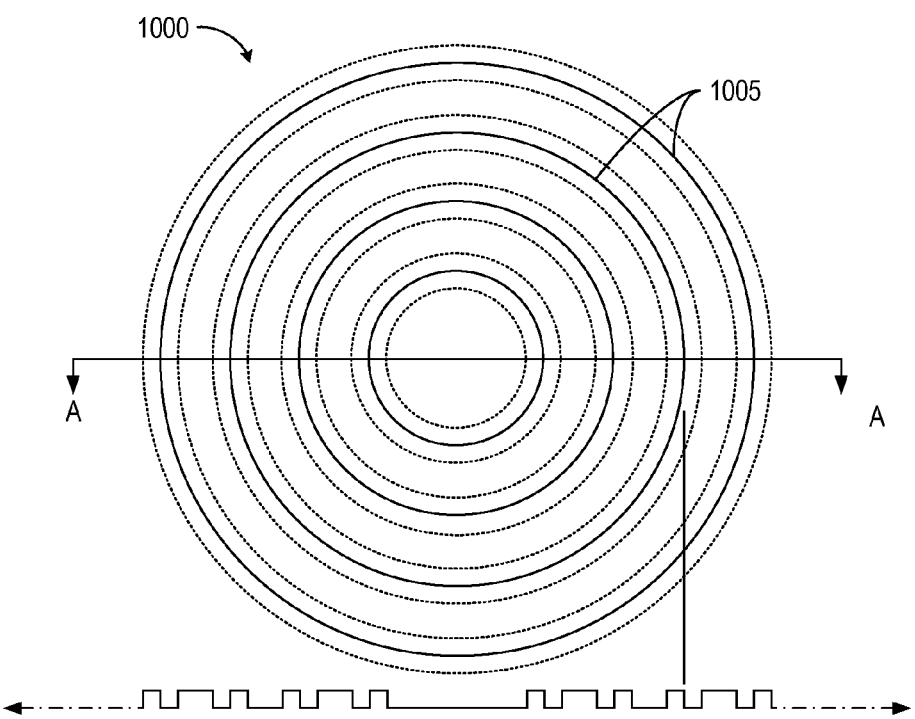
FIG. 10 is a plan view of a grating 1000 in accordance with an embodiment with concentric boundaries of odd symmetry 1005, and includes a cut-away view along line A-A.

FIG. 10 is a plan view of a grating 1000 in accordance with an embodiment with concentric boundaries of substantially odd symmetry 1005, and includes a cut-away view along line A-A. In this example the widths of the feature segments are discrete and the angles are continuous. The spacing of grating 1000 appears consistent, but may be varied to allow for sharp focus for a range of wavelengths, angles of incidence, or manufacturing variations.

Figure 11:
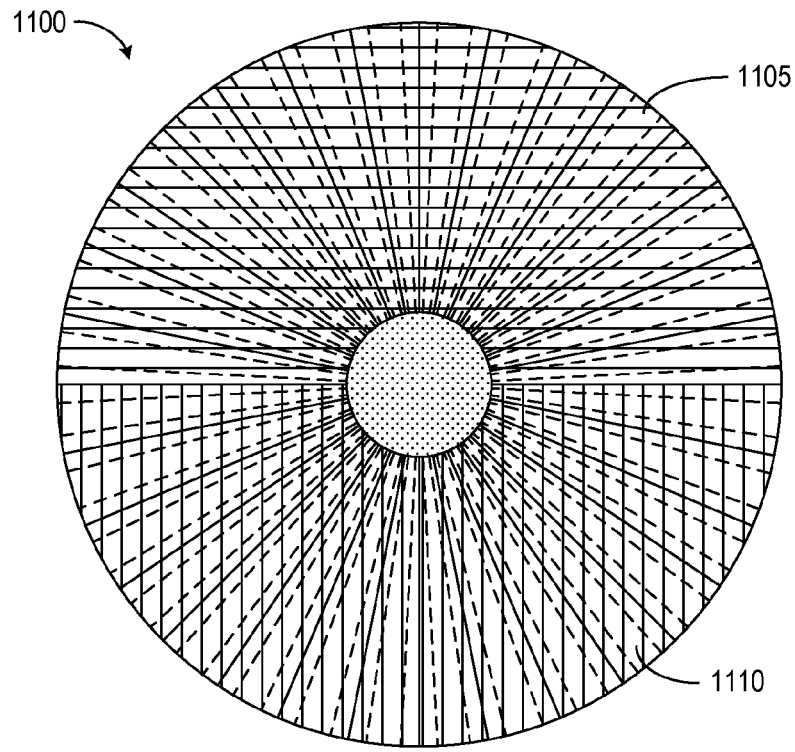
FIG. 11 is a plan view of a grating 1100 in accordance with an embodiment similar to grating 900 of FIG. 9.

FIG. 11 is a plan view of a grating 1100 in accordance with an embodiment similar to grating 900 of FIG. 9. The two halves of grating 900 provide essentially the same information. Grating 1100 adds half-circle polarization filters 1105 and 1110 with perpendicular orientations. Each half of grating 1100 thus produces image data specific to one of two polarizations, and these data can be used separately or together. More or fewer filters, with the same or different orientations, may be used in other embodiments. Different types of filters can also be used to cover all or a portion of gratings of the type described herein.

Figure 12:
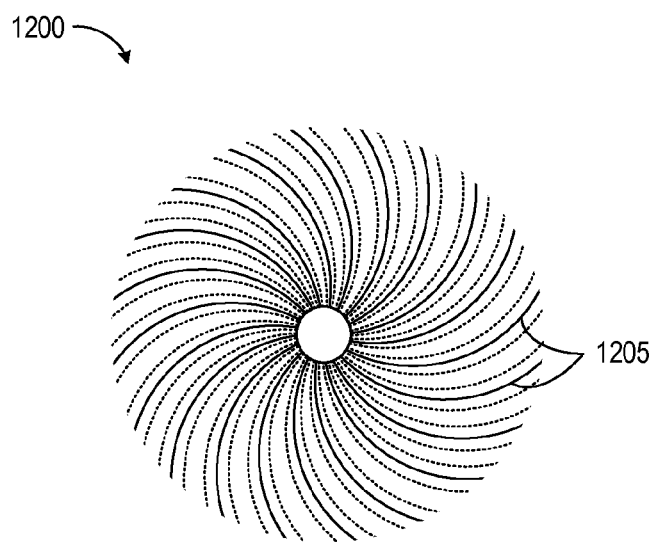
FIG. 12 is a plan view of a grating 1200 in accordance with another embodiment.

FIG. 12 is a plan view of a grating 1200 in accordance with another embodiment. Curved boundaries of odd symmetry 1205 extend radially from the center of the grating, and the widths of the feature segments widen gradually away from the center. The curvature of boundaries 1205 provide continuously varying angular information similar to what is available from grating 1000 of FIG. 10 while retaining the continuously varying spacings of grating 900 of FIG. 9.

Figure 13:
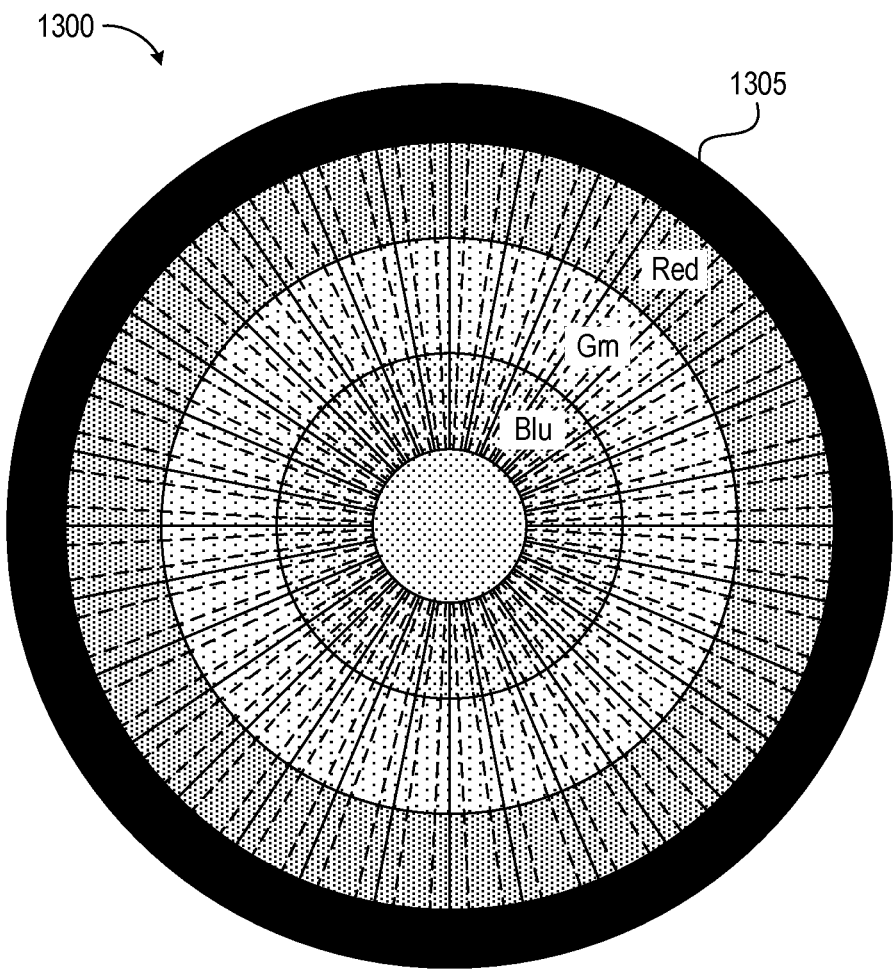
FIG. 13 depicts a grating 1300 in accordance with another embodiment.

FIG. 13 depicts a grating 1300 in accordance with another embodiment. As noted previously, different widths of the grating features provide sharper focus for different colors of light within the wavelength band of interest. Grating 1300 has the same radial symmetry of grating 900 of FIG. 9, but those areas for which the spacing is optimized for blue, green, and red light are provided with filters to admit their respective wavelengths. Omitting wavelengths that provide a blurred interference pattern on the underlying analyzer can improve image sharpness, and can allow more accurate reconstruction of color image data. Grating 1300 is bounded by an opaque mask 1305 that defines the limit of the aperture.

Figure 14:
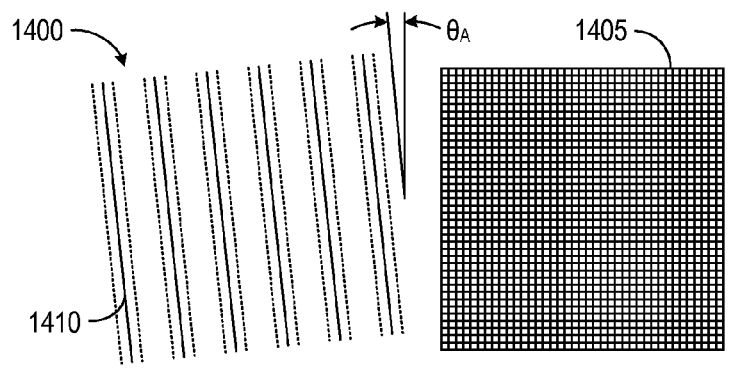
FIG. 14 depicts a grating 1400 and associated photodiode array 1405.

FIG. 14 depicts a grating 1400 and associated photodiode array 1405. Grating 1400 has parallel odd-symmetry boundaries 1410, which may have features of the same or different widths, or of varying widths along one or more boundaries. Parallel boundaries with the requisite diversity of widths and spacings to sample a sufficient number of spatial frequencies can image one-dimensional images, e.g., barcodes. Array 1405 is shown alongside, rather than below, grating 1400 to highlight the angle $\theta_A$ between the direction of boundaries 1410 and the columns of photosensitive elements in array 1405. Angle $\theta_A$ creates more diversity of measurements because the linear shadow covers different percentages of pixels in different rows. In one embodiment angle $\theta_A$ is selected so that the top of each boundary is offset from the bottom by about one pixel of array 1405.

Figure 15:
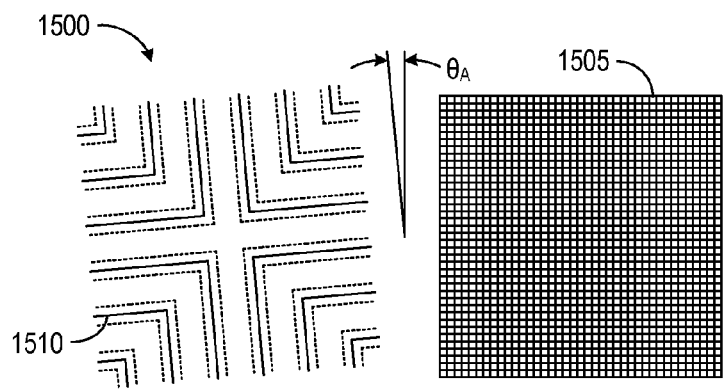
FIG. 15 depicts a grating 1500 and associated photodiode array 1505.

FIG. 15 depicts a grating 1500 and associated photodiode array 1505. Grating 1500 has parallel, right-angled boundaries 1510, which may have features of the same or different widths, or of varying widths along one or more boundaries. Parallel boundaries with the requisite diversity of widths and spacings along two dimensions to sample a sufficient number of spatial frequencies can image e.g. point sources, such as to identify the position of the sun, a fiducial LED, or a retroreflective element or patch used for motion capture. Angle $\theta_A$ can be introduced for the reasons presented above in connection with FIG. 14. Point source identification may also be accomplished with a grating that is also suitable for an imaging function.

Figure 16:
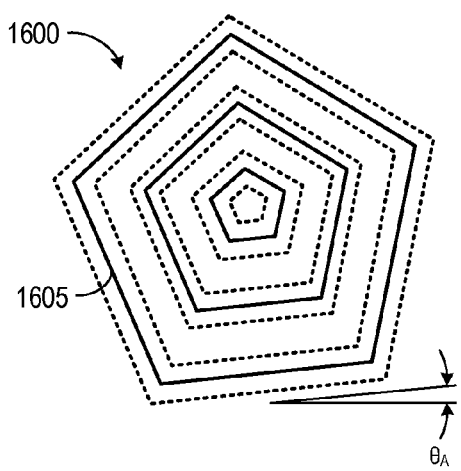
FIG. 16 is a plan view of a grating 1600 in accordance with an embodiment with pentagonal boundaries of odd symmetry 1605.

FIG. 16 is a plan view of a grating 1600 in accordance with an embodiment with pentagonal boundaries of odd symmetry 1605. In this example the widths of the feature segments are discrete, but they can vary along one or more boundaries in other embodiments. Straight boundaries may be advantageous over curved ones because line segments can more easily provide precise odd symmetry.

Grating 1600 provides information at five different orientations. Other boundary shapes, such as other polygons, are used in other embodiments. In general, polygons with odd numbers of sides provide greater orientation diversity than polygons with a similar but even number of sides (e.g., a pentagon provides more orientation diversity than a square or a hexagon).

Figure 17A:
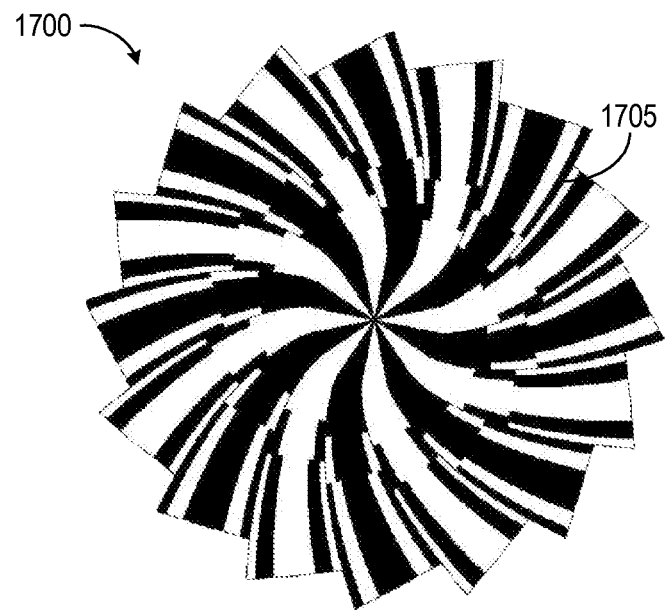
FIG. 17A is a plan view of a grating 1700 in accordance with another embodiment.
Figure 17B:
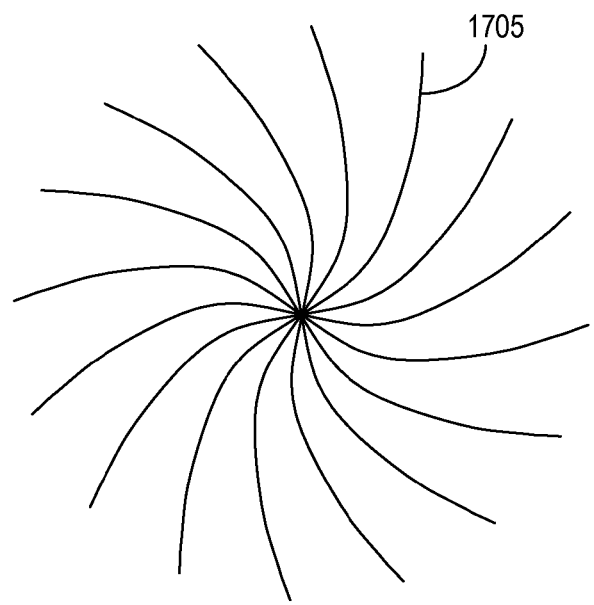
FIG. 17B depicts the shapes of boundaries 1705 of FIG. 17A.

FIG. 17A is a plan view of a grating 1700 in accordance with another embodiment. Recalling that relatively narrow (wide) segment spacing works better for relatively high (low) frequencies, feature spacing increases along odd-symmetry boundaries (between dark and light regions) with distance from the center. Curved boundaries of odd symmetry 1705 extend radially from the center of the grating to the periphery, radiating out between the dark (elevated) and light (recessed) arms near the center. The curved boundaries are obscured by grating features in FIG. 17A, so the shapes of boundaries 1705 are depicted in FIG. 17B for ease of review.

The segment widths do not continue to increase with radius, as there is a maximum desired width for a given wavelength band of interest (e.g., the widest may correspond to the lowest frequency of visible red light). The features that define boundaries 1705 therefore exhibit discontinuities as they extend toward the periphery of grating 1700. In this example, grating 1700 has three discrete areas each tuned to a subset or all of the wavelengths in the band of interest.

Figure 18:
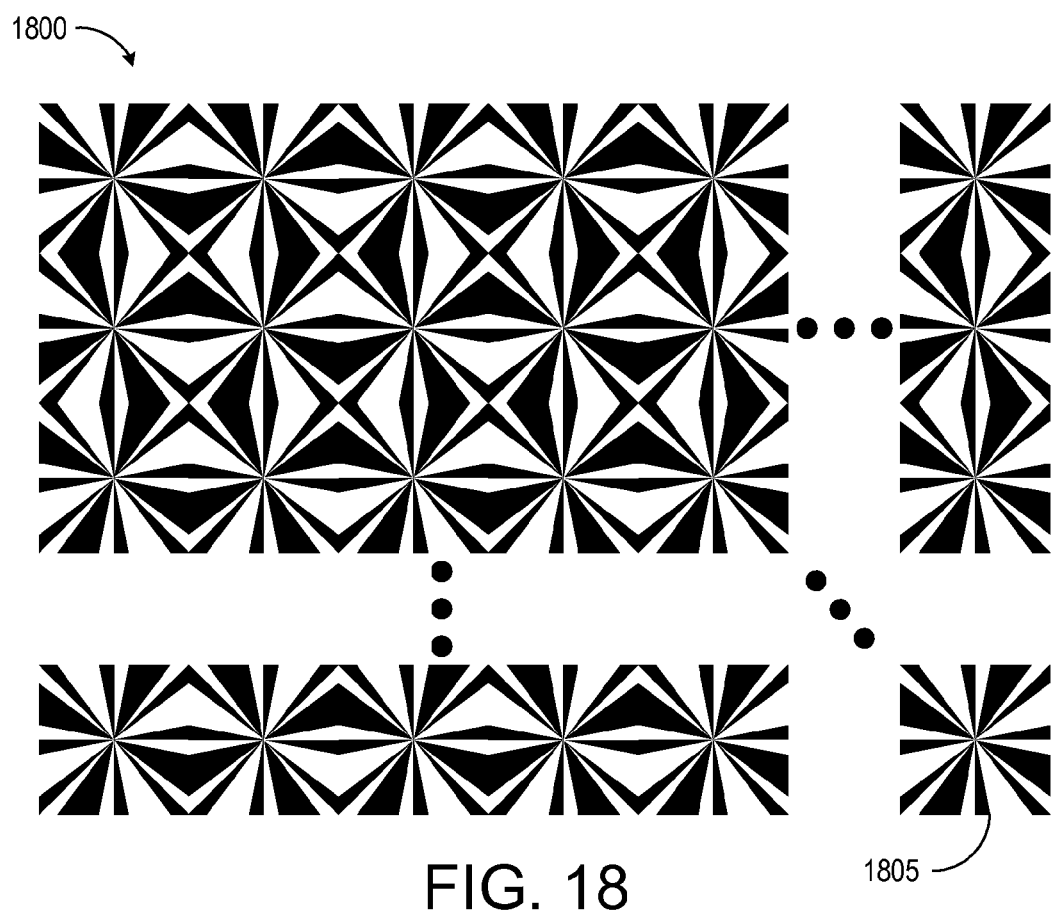
FIG. 18 depicts a two-dimensional array 1800 of gratings 1805 disposed over a photodiode array (not shown).

FIG. 18 depicts a two-dimensional array 1800 of gratings 1805 disposed over a photodiode array (not shown). Each of gratings 1805 is identical, but any number of parameters, many of which are discussed above, can be varied within and among gratings 1805. For example, different shapes and types of gratings can be used to create and image different types of interference patterns that can be combined or used separately to obtain some desired result. The decision to consider all or a specific subset of information generated by one or more of the constituent gratings can be done once, such as at time of manufacture to accommodate process variations, or can be done dynamically to highlight different aspects of a scene. Emphasizing aspects of different patterns can be used, for example, to highlight light of different polarizations, wavelengths, or angles of incidence.

Spaced gratings facing the same direction, particularly when their characteristics are well matched, can be used to sense moving objects. Assuming matched gratings with a fixed separation receiving light from the same scene, the difference between the photocurrents of the respective analyzer layers is sensitive only to objects relatively close to the pair. Further, the time derivative of this difference is sensitive to nearby, moving objects, and is insensitive to relatively distant moving or stationary objects.

Figure 19:
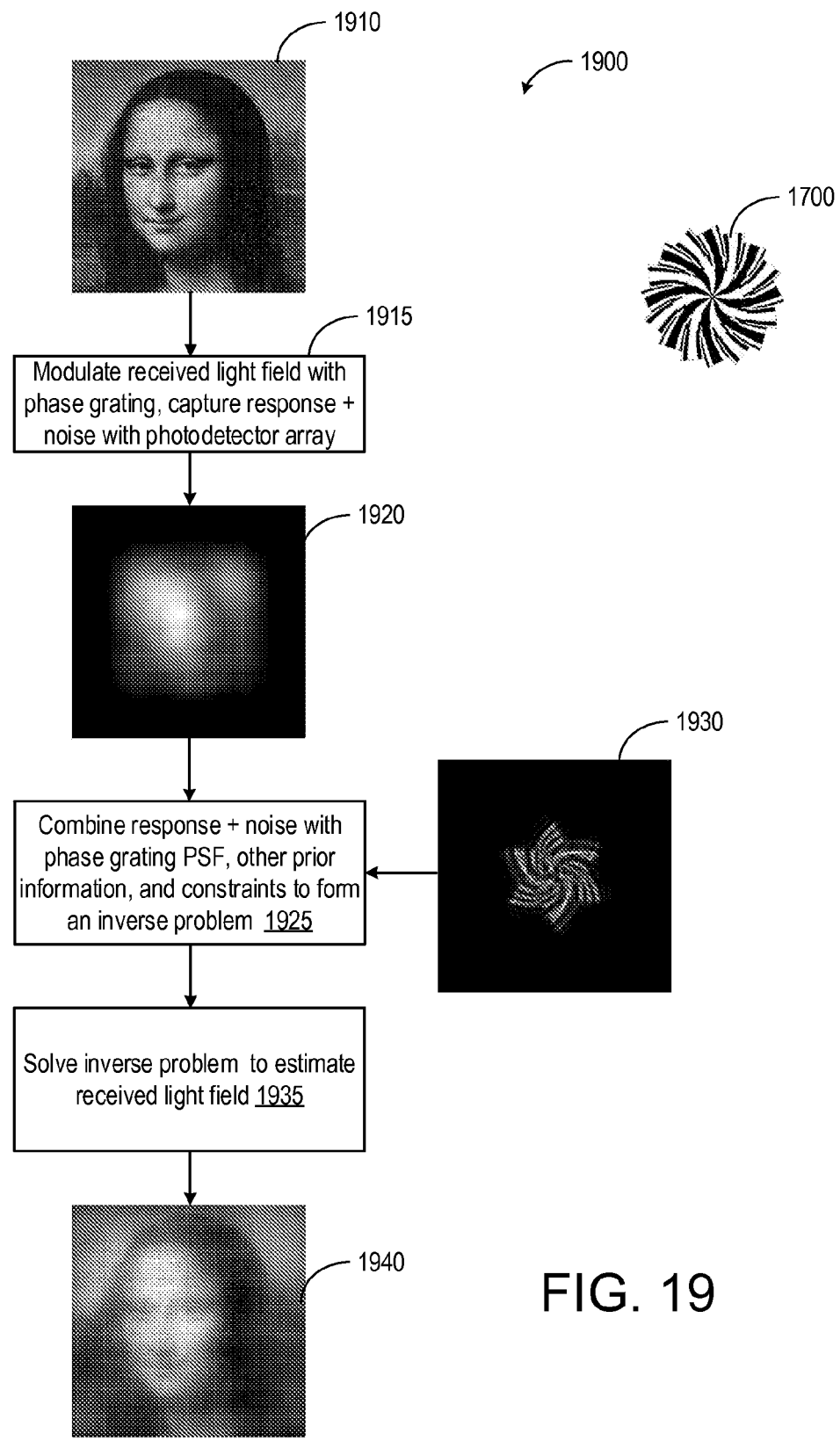
FIG. 19 is a flowchart 1900 detailing how an image 1905 is captured and resolved in accordance with grating 1700 of FIG. 17.

FIG. 19 is a flowchart 1900 detailing how an image 1905 is captured and resolved in accordance with grating 1700 of FIG. 17. First, an image 1910 is presented such that light from image 1910 is incident grating 1700. The incident light passes through phase grating 1700 to produce an intensity pattern 1920 on an underlying two-dimensional array of photosensors (not shown), which captures the pattern (1915). The captured pattern 1920 may appear unintelligible to a human; however, because grating 1700 has sharp features in its point-spread function (PSF), the pattern contains rich information about the image.

The PSF of grating 1700, possibly in combination with the underlying array, is known from a prior calibration or high-fidelity simulation. The way in which the PSF varies as a function of incident angle and color may also be similarly determined. This information is represented by a response 1930. A mathematical conversion based on this response can thus be used to reconstruct image 1910 from pattern 1920.

To recover the original image, responses 1920 and 1930 are combined to form an inverse problem (1925), which is solved (1935) to recover a version 1940 of the original image. One embodiment employs the well-known Tikhonov regularized inversion technique to accomplish steps 1925 and 1935. Take as a starting point a) detailed knowledge of the PSF of grating 1700, b) knowledge of the noise level of the system under current illumination conditions, and c) the specific readings observed for this image (pattern 1920). Express the unknown image as an N×1 vector x, where N is the total number of pixels one wishes to reconstruct. Express the readings from the photosensor as an M×1 vector y, where M is the total number of photosensors in the array. Express detailed knowledge of the PSF as an M×N matrix A such that for any image x, the formula yielding expected observed signal y under x is y=Ax, called the "forward equation."

To reconstruct an image, it suffices to solve the forward equation with a known measurement vector y for an unknown image x as follows. Multiply both sides of the forward equation by $A^T$ (the transpose of A) to obtain $A^T$ y=$A^T$ Ax. The matrix $A^T$ A is square and in principle could be directly inverted to recover x; however usually this inversion is poorly conditioned when noise is present and when not all eigenvectors of $A^T$ A have equally large associated eigenvalues. Thus in practice, Tikhonov regularization (as follows) usually delivers preferable results.

Next, select a regularization parameter λ>0 based on the noise level at the current illumination conditions. Finally, invert the matrix ($A^T$ A+λI) (where I is the identity matrix), assume ($A^T$ A+λI)≈($A^T$ A) and multiply on the left of the preceding equation to obtain x≈$(A^T A+\lambda I)^{-1} A^T$y. Therefore, for a given regularization parameter X, the image recovered through Tikhonov regularization is a linear combination of the readings from the photosensor. If the PSF is sufficiently spatially invariant to the extent that its spatial dependence can be neglected, these computations can be done in the Fourier domain, allowing for much faster numerics.

Another embodiment recovers the matrix x using compressed sensing. If the scene is expected to be sparse in some basis (such as a wavelet transform W for natural images), the following methodology can be used. We can recover the sparse scene components z where x=Wz by finding the z that minimizes the following cost function: ½ $r^T r+\lambda f(z)$, where r is the residual (y−AWz), λ>0 is a regularization parameter (different from that used in Tikhonov regularization, but also noise-dependent), and f(z) is a function penalizing non-sparse z. If f(z) is a convex function of z such as the $L_1$ norm, this optimization problem can be solved efficiently using convex optimization techniques. The penalty function f(z) can also take on other forms, including terms penalizing total variation in the reconstructed image x or other prior scene knowledge.

Some of the chief advantages of compressed sensing over linear approaches such as Tikhonov regularization are that the former allow more prior information about the expected scene structure to help shape the final image. Further, if $A^T$ A does not have full rank or cannot measure certain aspects of the scene (for example, due to some near-zero regions of the 2D Fourier transform of the PSF), using compressed sensing sometimes overcomes these limitations given correct prior information about the expected images.

The foregoing Tikhonov and compressed-sensing techniques can include iterative methods to reduce problem complexity. For example, Richardson-Lucy deconvolution can iteratively approximate Tikhonov regularized inversion and iterated wavelet thresholding can be a numerically-efficient way to converge to a compressed-sensing-like solution.

In some embodiments the purpose of the sensor is not to reconstruct an image, but to perform some optical sensing task. In such cases the vector x may represent the sought measurement rather than the field of image pixels, and the forward transform A can be appropriately modified.

Figure 20:
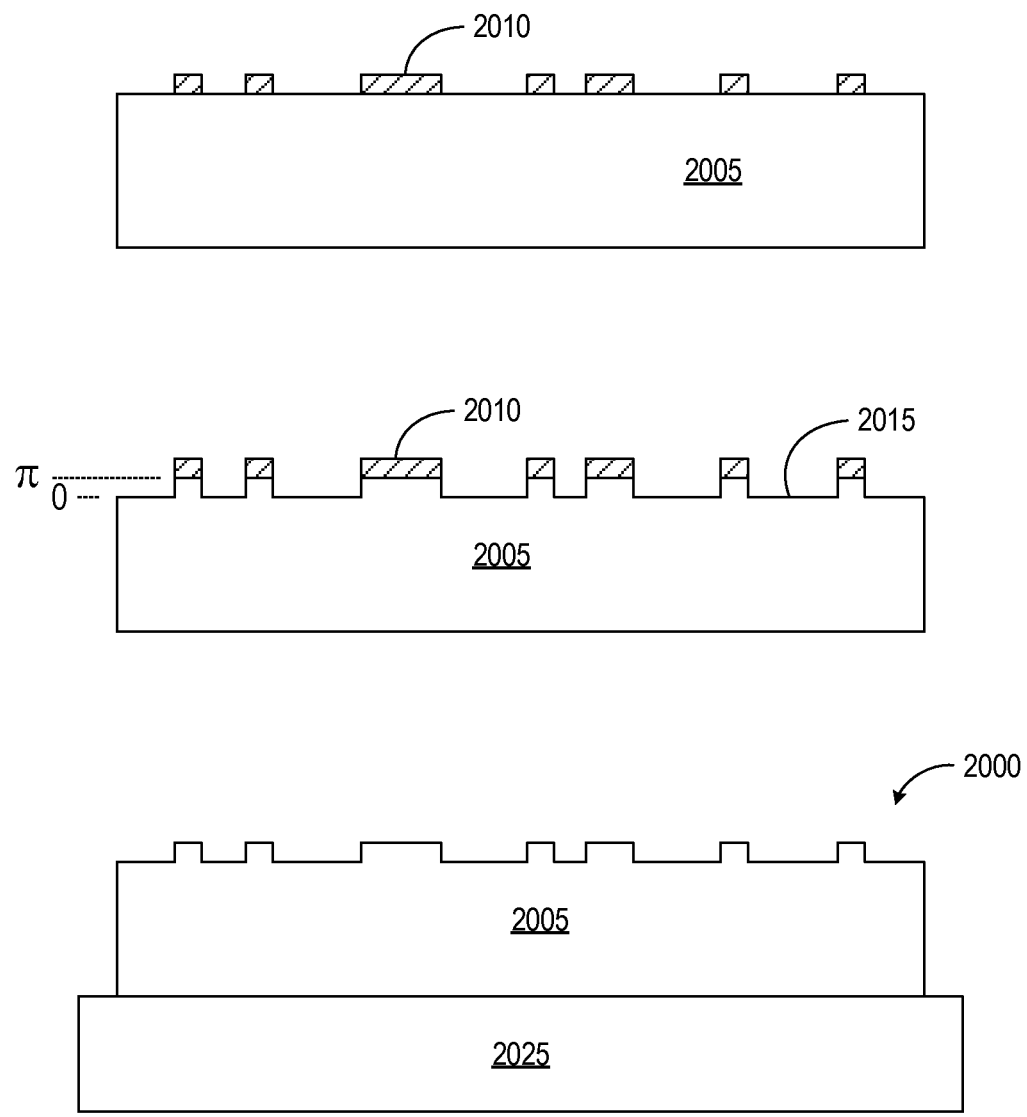
FIG. 20 depicts lithographic process for forming an image sensor 2000 in accordance with one embodiment.

FIG. 20 depicts a lithographic process for forming an image sensor 2000 in accordance with one embodiment. First, a wafer 2005 of material that is transparent over the wavelength band of interest is patterned with a mask 2010 that defines the relatively high features of what will become an odd-symmetry grating surface of the type detailed herein. Next, the exposed surface of wafer 2005 is etched to create recessed regions 2015. Mask 2010 is then removed. Finally, wafer 2005, now comprising a grating, is bonded to a photodiode array 2025. Photolithographic and wafer-bonding processes are well known to those of skill in the art, so a detailed discussion is omitted.

FIG. 21A depicts a camera 2100 in accordance with an embodiment in which a converging optical element, in this case a lens 2105 (although a single-element lens is shown for simplicity of illustration, generally the optical element can comprise one or more refractive, diffractive, and/or reflective elements), is used in conjunction with a phase grating element, grating 2110, disposed in the path between the optical element and a dense photodetector array 2115 to form images thereon. A scene incident the front side of lens 2105 is projected through grating 2110 and onto array 2115. Grating 2110 induces spatial modulations in the incoming light and passes the resulting interference pattern to array 2115, which captures a digital representation of the spatial modulations. An integrated processor 2120 electrically coupled to array 2115 computes an image of the scene from the digital representation. The processor is shown also physically coupled to array 2115, but the processor can be located elsewhere in other embodiments.

Lens 2105 defines a front focal point FFP and a rear focal point RFP, and is spaced from grating 2110 by a distance less than the image-plane distance D between lens 2105 and focal point RFP. Array 2115 is on the opposite side of focal point RFP from grating 2110 in this example. Grating 2110 may be an odd-symmetry grating that has properties detailed above in connection with the preceding figures. In other embodiments (such as an embodiment primarily operating in a macro mode) the focal length of lens 2105, defined for objects at infinity, may be closer to lens 2105 than to grating 2110, or may move over a range that encompasses such relative positioning.

Surface features of grating 2110 are separated from array 2115 by a distance X. Though shown as separate structures for ease of illustration, grating 2110 can be integrated with or attached to array 2115. Distance X in camera 2100 is, in this example, no more than 400 times a longest wavelength of interest $\lambda_{max}$ in the medium(s) between the surface features of grating 2110 and array 2115 ($X \leq 400\lambda_{max}$). For example, a camera in which $\lambda_{max}$ is 0.5 microns may have a spacing X between the features of grating 2110 and the surface of array 2115 of up to 200 microns.

FIG. 21B is an example of camera 2100 with a point source 2125, represented by tip of an arrow, that is imaged in focus on array 2115. Grating 2110 is out of the focal plane, so the light from lens 2105 presents a blur-spot PSF 2130 to grating 2110. (As in other examples used herein, the area occupied by PSF 2130 refers to the area of the central lobe.) Grating 2110 produces an interference pattern from function 2130, but the illumination boundaries of the pattern are not evident in the tightly focused, diffraction-limited spot 2135 on array 2115. Objects at the range and position of point source 2125 are tightly focused (field curvature and other aberrations may change the best focus range for other positions), and are nominally imaged at the full resolution of array 2115, assuming lens 2105 is capable of such resolution.

FIG. 21C is an example of camera 2100 with a point source 2140 that is imaged out of focus on array 2115. As in the prior example, the light from lens 2105 presents a blur-spot PSF 2145 to grating 2110, and grating 2110 produces a pattern of spatial modulations. Because point source 2140 is imaged out of focus, however, the area of PSF 2150 at array 2115 is greater than in the example of FIG. 21B, and illumination transitions/substructure within the pattern area are evident. In camera 2100, these illumination transitions are near-field spatial modulations induced by features of grating 2110. The resultant spiral pattern of PSF 2150 is preferably an invertible orientation chirp. As used herein, an "orientation chirp" is a pattern of spatial modulations that cover ranges of spatial frequencies and orientations sufficient to recover an image at a desired resolution.

FIG. 21D is an example of camera 2100 with a point source 2155 that is imaged more out of focus than point source 2140 in the example of FIG. 21C. Light from lens 2105 presents a blur-spot PSF 2160 that is still greater than PSF 2145, and a resultant invertible PSF 2165 on array 2115 is similarly larger than PSF 2150. Although not shown, imaging a point source at the FFP of FIG. 21A produces an invertible PSF including orientation chirp features. Two point sources, one in front of and one behind point 2125 but along the same optical axis, may produce similar-sized orientation chirps. Due to aberrations in the lens system, however, the chirps may differ—such differing characteristics may be used to resolve range, as detailed further below.

FIGS. 21A-D illustrate the general point that the pattern area and the richness of the accompanying spatial modulations on array 2115 are a function of focus, the duller the focus the greater the area and the better resolved the spatial modulations. Point sources farther away from lens 2105 than point source 2125 of FIG. 21A produce ever larger PSFs on the array as they move away from (or towards) lens 2105.

The PSF for an out-of-focus point source is a scaled version of an orientation chirp from grating 2110, where the diameter of the orientation chirp is proportional to defocus of the point source. The observations at the sensor plane (the surface of array 2115) will therefore be the in and out-of-focus imaged points, each convolved with the orientation chirp at a chirp phase dependent upon the position the light ray bundle received from that point, scaled according to an out-of-focus parameter, and spatially superimposed with like contributions from other imaged points. Camera 2100 can recover relatively high-resolution images of out-of-focus objects because this convolution is computationally invertible for the majority of common image capture situations. In this context, "computationally invertible" means that image data can be recovered to a specified degree of precision using e.g. inverse, pseudoinverse, and compressed-sensing transformations. A PSF is computationally invertible, for example, if its 2D Fourier transform is "complete," or has substantial amplitude at all spatial frequencies required to recover an image at a specified resolution.

Not all spiral PSFs are complete. For example, Archimedean spirals have regularly spaced arms whose Fourier transforms have peaks at the reciprocal of the inter-arm period and nulls between these peaks. In contrast, the spiral PSF 1930 of FIG. 19 has few, unevenly spaced arms that are sharply bounded and sweep through all orientations, so it has significant Fourier power at all spatial frequencies and is complete. Due to this completeness, accurate deconvolution is relatively well-conditioned, so undoing the effect of the PSF is relatively straightforward. Regardless of whether computations are performed in the Fourier domain or the spatial domain, deconvolution works well if the Fourier transform of the PSF has no zeros. In the case that a point source causes a blur spot 2160 that is not concentric with a spiral, the resulting PSF will contain a spatially wrapped version of the PSF. Spatially wrapping the spiral does not substantially affect its completeness.

Camera 2100 can measure light intensity from photodetector array 2115 without first needing to focus (although some embodiments can focus manually or automatically). Data captured by array 2115 includes orientation chirps with Fourier-component strengths that vary with depth (see FIGS. 21B-D). The Fourier transform of the local observations will be the product of the imaged object's Fourier transform and the depth-dependent Fourier transform of the orientation chirp. By searching for the depth-specific kernel that best matches this product for each imaged point, scene depth can be determined, assuming the scene has some texture, as detailed below.

The depth d of a local scene patch x can be inferred from readings y through Bayesian estimation as follows. First, a likelihood p(y|d) of each depth can be computed by a further Bayesian estimation based on knowledge that the Fourier transform of y is the product of the Fourier transforms of x and the depth-dependent PSF, and with knowledge of typical power spectra of photographed objects. Next, this likelihood p(y|d) is weighted by a Bayesian prior on the known distribution of depths and depth changes in a scene to arrive at a posterior probability of p(d|x) for depth at each point in the scene. Bayesian estimation of the depth map of a scene based on depth and depth change priors, as well as point-wise estimates of depth associated with corresponding certainty (indicated by the height of peaks in the likelihood p(y|d)) is a technique known to those skilled in the art, and will not be further discussed here. In this application, knowledge of the true depth map is important for accurate image recovery (to be described shortly) precisely for those images that have significant Fourier power in spatial frequencies that interact with the Fourier transform of the PSF. Thus, accurate depth maps are possible where the scene has fine texture, and where scene patches lack this texture convolution with the PSF does not degrade image quality in the scene.

Next, the Fourier transforms are deconvolved in image space or the Fourier domain; the problem scale will dictate which of these is faster. The deconvolution kernel can also be made to vary with light level for a Weiner-optimal reconstruction (although humans tend to prefer overly-sharpened images; this sharpening filter can be incorporated with the deconvolution filter to save an additional step).

The result of selecting the correct filter followed by deconvolution is a depth map and a reconstruction of the original image. If the orientation chirp is Fourier-complete, the reconstructed image can resolve the same number of pixels as array 2115. This is unlike most plenoptic cameras, and is made possible by the fact that each pixel reading contributes useful information to the deconvolution problem. In the case where a PSF's high-frequency components are small, processor 2120 may smooth the highest spatial frequencies to avoid adding too much noise. In low-light conditions, camera 2100 may lose e.g. a factor of two in resolved pixels due to this effect; this represents an improvement over existing plenoptic cameras, whose pixel efficiency may be as low as 4%. For well-formed orientation chirps according to an embodiment and general imaging conditions, PSFs with a central lobe diameter up to six photodetector pitches should be invertible to recover image features with a spatial frequency up to at least 0.25 cycles per photodetector (Nyquist frequency being 0.5 cycles per photodetector pitch in the major dimensions of the photodetector array). Such performance depends in part on the lens element having a sufficient modulation transfer function at the relevant spatial frequencies.

Figure 22:
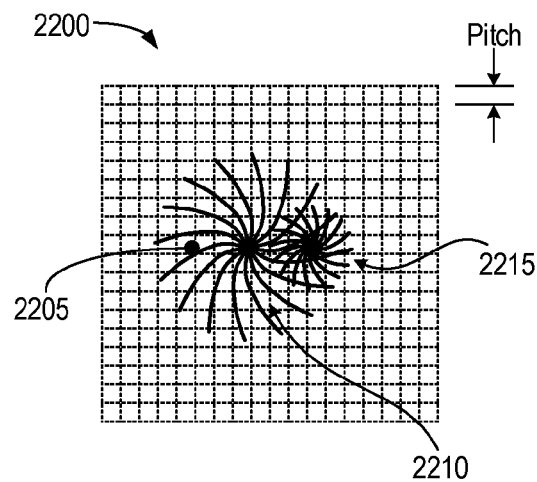
FIG. 22 is a plan view of a portion of an array of pixels 2200 illuminated with three PSFs 2205, 2210, and 2215.

FIG. 22 is a plan view of a portion of an array of pixels 2200 illuminated with three PSFs 2205, 2210, and 2215. PSF 2205 is an orientation chirp representing a sharply focused point source; illumination substructure cannot be resolved given the pitch of array 2200. If all points of a given scene are in focus, image resolution is primarily a function of array pitch, or of array pitch and the diameter of a diffraction-limited spot.

PSF 2210 is an orientation chirp representing a poorly focused point source; spatial modulations appear as spiral arms of a computationally rich PSF that can be resolved by array 2200 to locate the corresponding point source in the image. Finally, PSF 2215 represents a point source whose focus is between those of PSFs 2205 and 2215; spatial modulations can again be resolved to locate the corresponding point source in the image.

For both PSF 2210 and 2215, the resolution of the image is limited by the larger of the pitch and the spacing of the separation between arms of the PSF spiral. In this illustration, the three point sources are easily located in the two dimensions of array 2200. Further, the three disparate pattern areas of the three PSFs provide a measure of distance in a dimension normal to array 2200. Cameras like camera 2100 of FIGS. 21A-D can therefore provide extended depths of field, focused images for out-of-focus objects, and measures of distance from image data.

Figure 23:
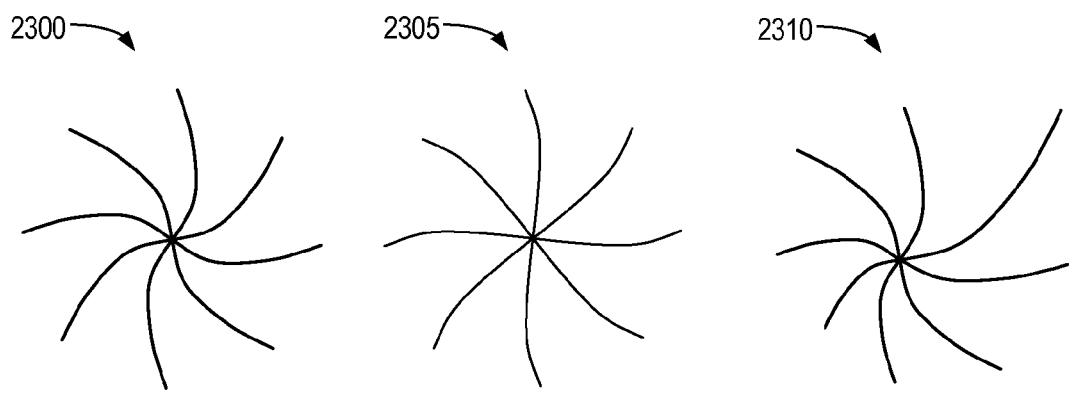
FIG. 23 depicts three spiral PSFs 2300, 2305, and 2310 to illustrate how cameras in accordance with some embodiments can compensate for lens aberrations, including spherical aberration, coma, and Petzval field curvature.

FIG. 23 depicts three spiral PSFs 2300, 2305, and 2310 to illustrate how cameras in accordance with some embodiments can compensate for lens aberrations, including spherical aberration, coma, and Petzval field curvature. Such compensation can simplify primary lens design and allow an increase in aperture without sacrificing image quality.

Spherical aberration is the condition whereby the focal length of a given annulus of a lens varies linearly with the annulus' radius. In the configuration of FIG. 21, this condition may influence the shapes of orientation chirps on the array. PSF 2300 of FIG. 23 is a hypothetical ideal chirp, the result of a perfect lens. PSF 2305 shows a type of chirp distortion that may result from a lens with spherical aberration. As compared with PSF 2300, PSF 2305 has relatively linear arms near the center. So long as the orientation chirp is complete (invertible to recover the image data), imaging performance will not be degraded. Even if not complete, imaging performance may be acceptable if the orientation chirp is sufficiently invertible to recover images to a desired resolution.

A lens has coma if light passing through different annuli centered on the lens forms annuli on the image sensor whose center varies with annulus radius. As shown in PSF 2310, coma produces an elongated and distorted, but complete spiral. Petzval field curvature is the aberration whereby the lens' focal surface is not planar. As with spherical aberration, coma, Petzval field curvature, and other aberrations can be undone if the orientation chirp is sufficiently complete.

Lens aberrations can be beneficial in some embodiments. A PSF out-of-focus to one side of the image plane can cover a pattern area of the same size as a PSF out-of-focus to the other side of the image plane. If two such PSFs are identical, then the camera may not be able to distinguish between them. Lens aberrations can render such PSFs distinguishable, however, such as by producing opposite asymmetries, and can therefore allow cameras in accordance with some embodiments to better distinguish point sources along the axis of incidence.

Figure 24:
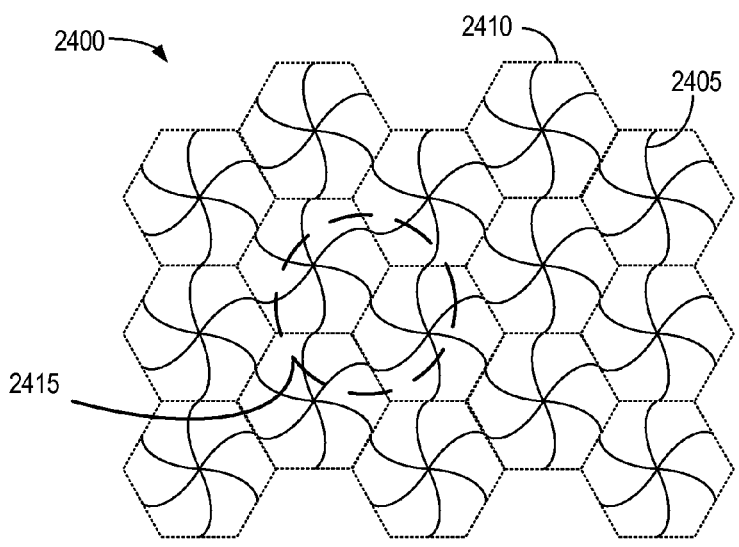
FIG. 24 depicts a tessellated optical element 2400 to illustrate aspects of phase gratings in accordance with some embodiments.

FIG. 24 depicts a tessellated optical element 2400 to illustrate aspects of phase gratings in accordance with some embodiments. Element 2400 is tessellated with spiral ensembles 2410 of sub-elements 2405—depicted as curvilinear boundaries—that are contiguous across tessellation borders (the hexagonal borders are for illustration, and do not represent physical structure in this example). The sub-elements of each ensemble are arranged such that light converged by element 2400 from a point source and passing through one of ensembles 2410 forms a PSF with spatial modulations representative of the ensemble. In one aspect, the tessellated optical element further converges what would otherwise strike a sensor array as a blurry PSF into a PSF that, while of similar size to the hypothetical PSF, contains high-frequency substructure.

Returning for a moment to the example of FIG. 21D, the blur spot PSF 2160 is assumed to be centered on an ensemble of spiral features to produce the spiral PSF 2165. This is a somewhat special case. Point sources at the same distance from the camera yet in general position will have a PSF containing all sub-elements 2405 of at least one ensemble 2410 collected from neighboring ensembles, with some of them spatially wrapped around. In the example of FIG. 24, a PSF outline 2415 represents the area of a central lobe that is off center with respect to any of the sub-gratings 2410, but that nevertheless covers enough grating features 2405 to produce an invertible orientation chirp. In general, it is beneficial that the wrapping of spatial features between ensembles 2410 not substantially alter the magnitude of the components of the Fourier transform of the resultant orientation chirp. A circle like outline 2415, of sufficient area to encompass one of ensembles 2410, can be swept along a path between neighboring ensembles while, for all intermediate circle positions along the swept path, the swept circle contains optical sub-elements arranged at all the orientations contained in the circle at the start of the path (e.g., ail positions produce similar spectra, but with shifting phase).

Figure 25:
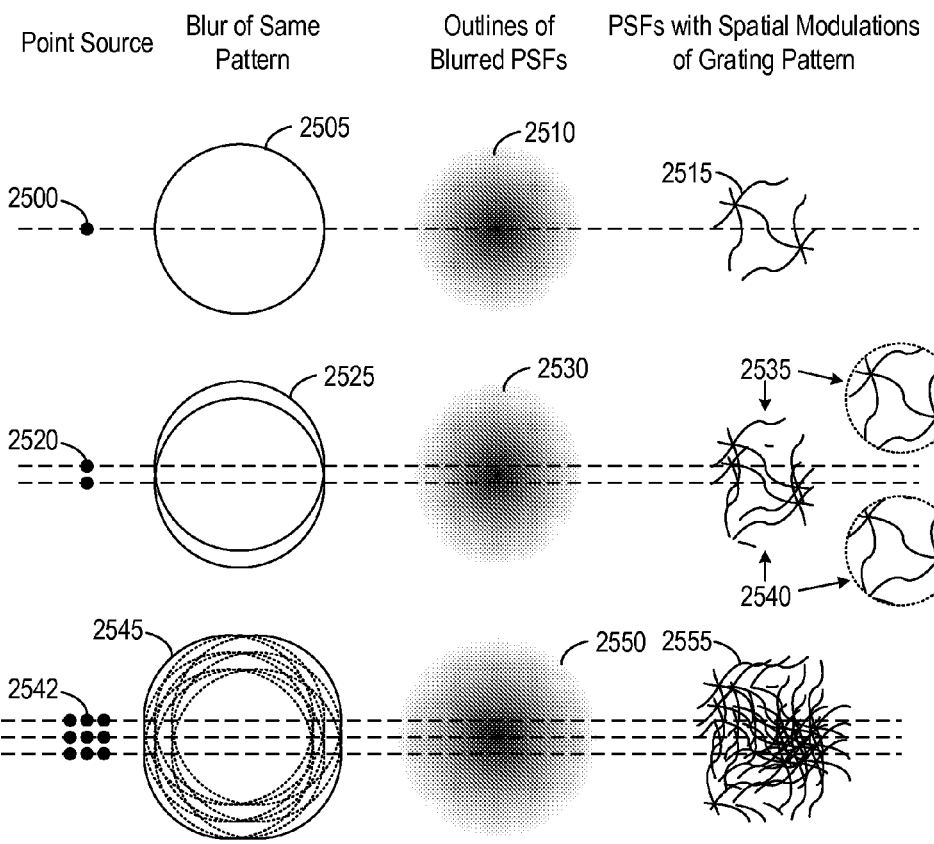
FIG. 25 depicts how the rich pattern of spatial modulations within orientation chirps produced by grating 2400 of FIG. 24 facilitates improved resolution for out-of-focus PSFs.

FIG. 25 depicts how the rich pattern of spatial modulations within orientation chirps produced by grating 2400 of FIG. 24 facilitates improved resolution for out-of-focus PSFs. As in other examples, the preceding digit or digits of each element name indicate the figure in which the element was introduced. Using this convention, elements 24## and 25## refer to features depicted in FIGS. 24 and 25, respectively.

In the top row of FIG. 25, light rays from a point source 2500 pass through a lens (not shown) and onto tessellated grating 2400 of FIG. 24 over the area 2505 encompassed by outline 2415 as blurred PSF 2510. The grating creates orientation chirp 2515, which includes a rich set of spatial modulations as a consequence of the sub-elements 2405 within the area of outline 2415. Chirp 2515 is not a spiral because PSF 2510 is not centered on an ensemble (the pattern of chirp 2515 is shown to match the pattern of sub-elements 2405 within the PSF outline 2415). However, the spatial modulations of chirp 2515 are sufficient that chirp 2515 is invertible.

The second row of FIG. 25 is similar to the first, but includes light rays from adjacent point sources 2520 that illuminate overlapping areas 2525 to produce a pair of overlapping, blurred PSFs 2530. The grating creates a discernible pair of orientation chirps 2535 and 2540, the locations of which can be computationally inverted to a higher resolution than could the smeared PSFs 2530. Chirps 2535 and 2540, shown separately to the right, are slightly different from one another because each PSF 2530 impinges upon a slightly different area of the grating.

The third row of FIG. 25 shows a constellation of nine point sources 2542 that illuminate an area 2545 on the grating with overlapping, blurred PSFs 2550, and the resultant nine orientation chirps collectively labeled 2555. As in the last example, the locations of the point sources corresponding to the orientation chirps 2555 can be resolved with far greater precision than could be accomplished using the PSFs 2550.

Figure 26A:
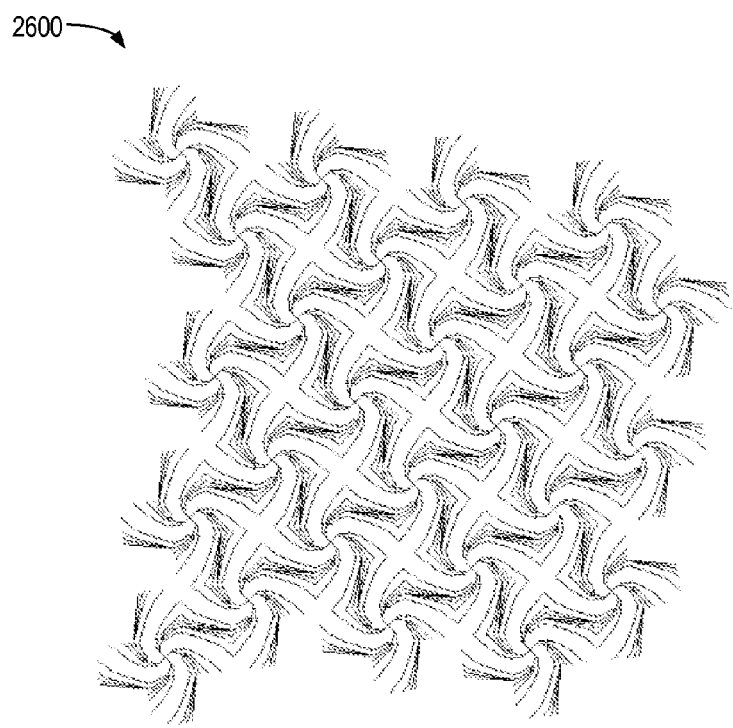
FIGS. 26A and 26B depict tessellated gratings 2600 and 2605 in accordance with some embodiments.
Figure 26B:
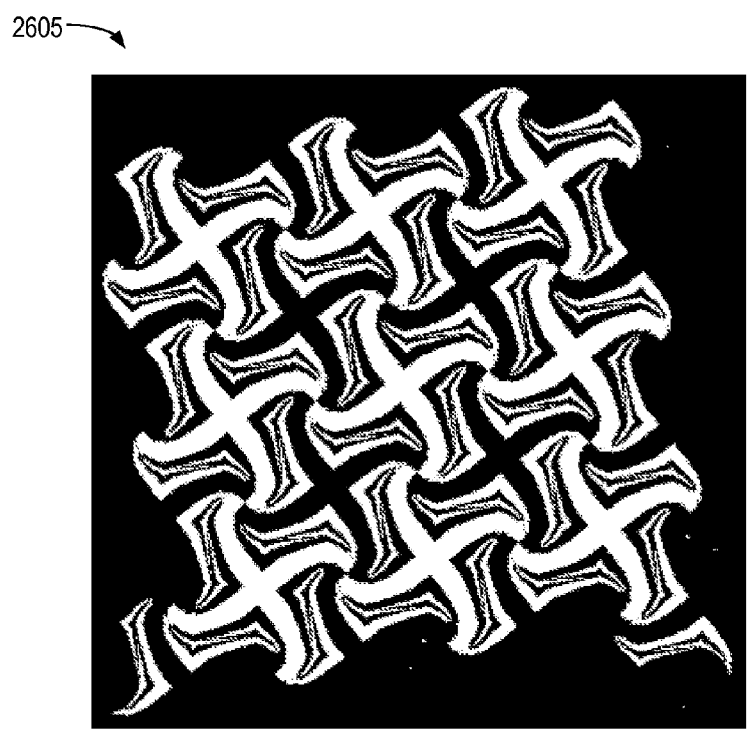

FIGS. 26A and 26B depict tessellated gratings 2600 and 2605 in accordance with some embodiments. Grating 2600 is depicted using boundaries between high and low features, whereas grating 2605 depicts relatively high and low features in black and white, respectively.

Figure 27A:
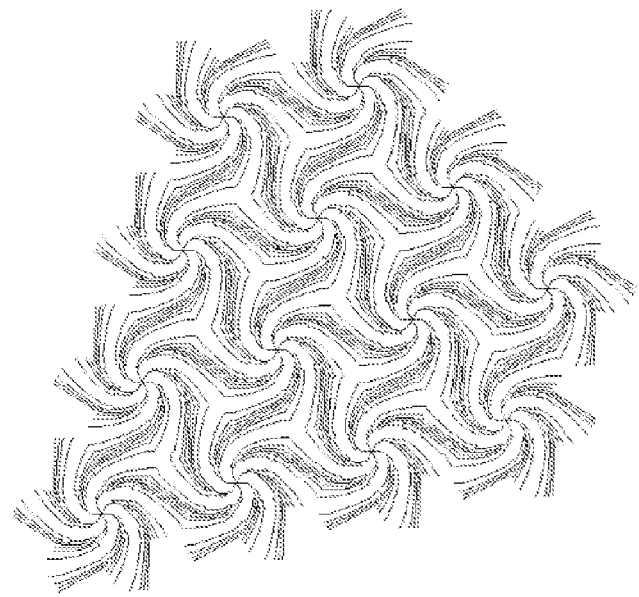
FIGS. 27A and 27B depict tessellated gratings 2700 and 2705 in accordance with some embodiments.
Figure 27B:
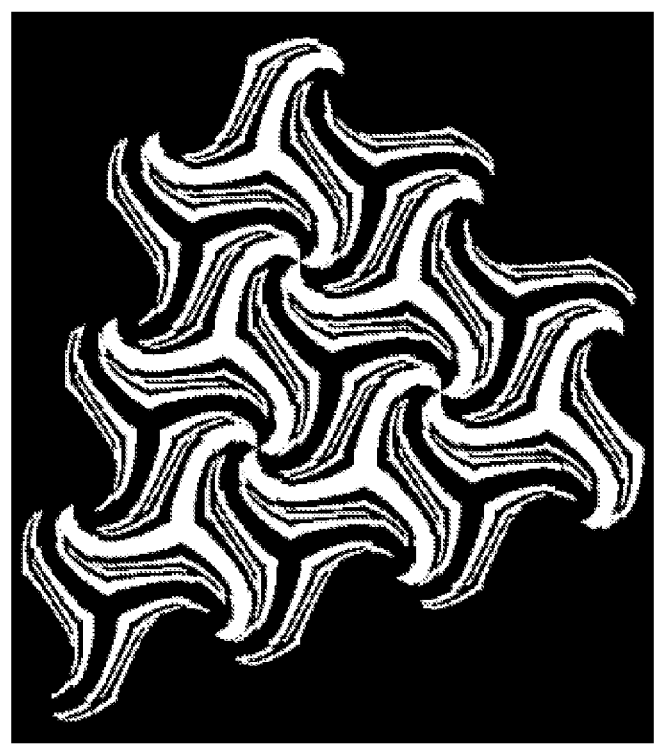

FIGS. 27A and 27B depict tessellated gratings 2700 and 2705 in accordance with some embodiments. Grating 2700 is depicted using boundaries between high and low features, whereas grating 2705 depicts relatively high and low features in black and white, respectively.

Figure 28:
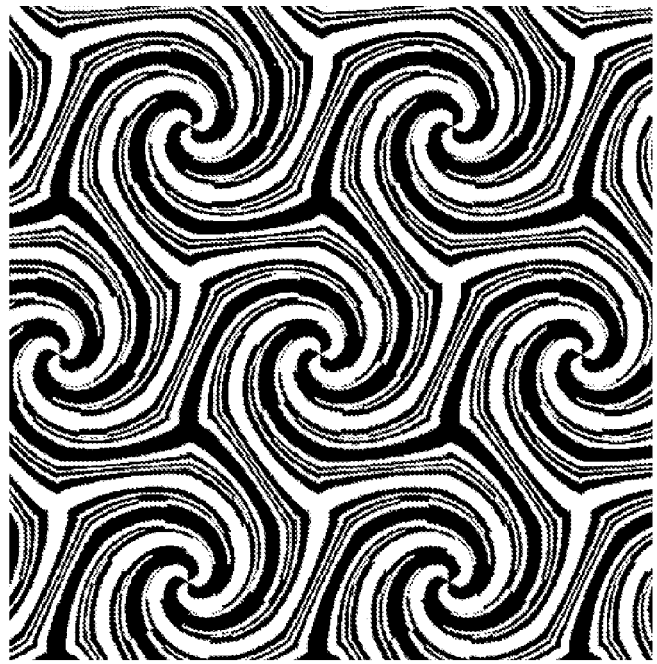
FIG. 28 depicts a tessellated grating 2800 in accordance with one embodiment.

FIG. 28 depicts a tessellated grating 2800 in accordance with one embodiment. Grating 2800 depicts relatively high and low features in black and white, respectively.

Figure 29:
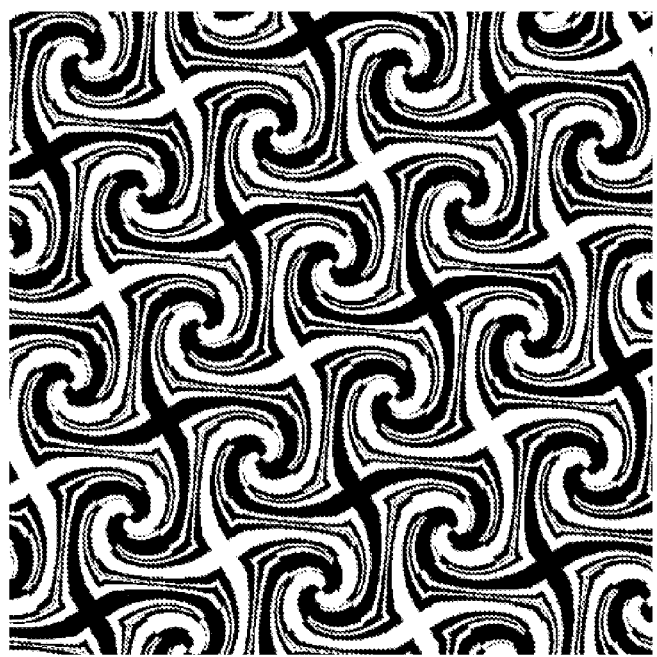
FIG. 29 depicts a tessellated grating 2900 in accordance with another embodiment.

FIG. 29 depicts a tessellated grating 2900 in accordance with another embodiment. Grating 2900 depicts relatively high and low features in black and white, respectively.

Figure 30:
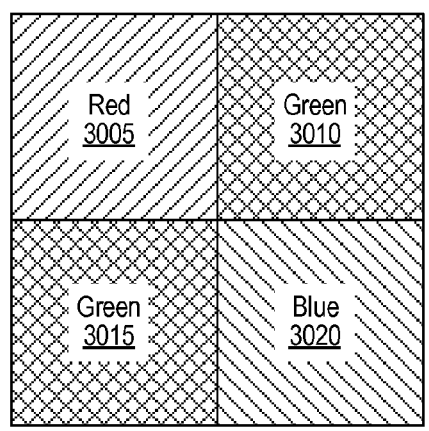
FIG. 30 depicts a filter array 3000 that can be used in accordance with some embodiments to produce color images using cameras of the type detailed in FIGS. 21A-D.

FIG. 30 depicts a filter array 3000 that can be used in accordance with some embodiments to produce color images using cameras of the type detailed in FIGS. 21A-D. Filter array 3000 includes four color filters, a red filter 3005, two green filters 3010 and 3015, and a blue filter 3020. Each filter is associated with what amounts to an instance of a camera like camera 2100 of FIG. 21A that acts as one of four color channels for the overall camera. For each camera like camera 2100, the wavelength band of interest is limited to the wavelengths passed by the color filter in the optical path.

Figure 31:
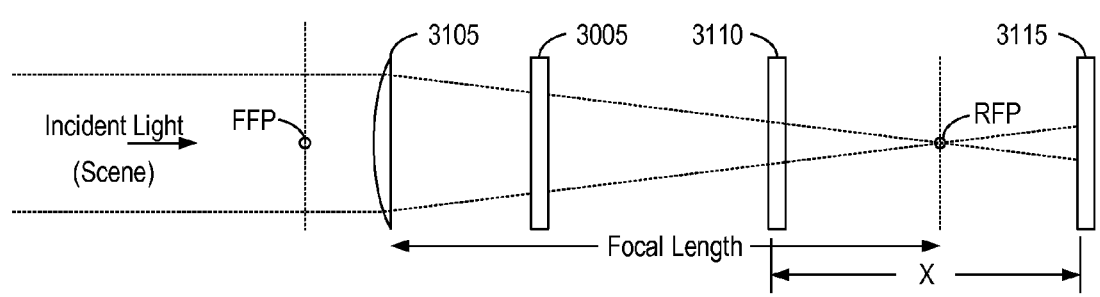
FIG. 31 depicts a color channel 3100, one of four color channels for the embodiment introduced in connection with FIG. 30.

FIG. 31 depicts a color channel 3100, one of four color channels for the embodiment introduced in connection with FIG. 30. Channel 3100 is similar to camera 2100 of FIGS. 21A-D, so a detailed discussion is omitted. Briefly, channel 3100 includes a color filter, a lens 3105 whose optical properties should be tuned for the light frequencies admitted by the color filter, a grating 3110, and a photodetector array 3115. The red filter 3005 of FIG. 30 is inserted somewhere in the optical path and covering the entire field of view, in this case between lens 3105 and grating 3110. Characteristics of channel 3100, such as the focal length of lens 3105, the spacing X between grating 3110 and array 3115, the spatial frequency range of grating 3110, the depth of grating features and composition of grating 3110, and the geometry of the grating sub-elements may be optimized for the selected color. An image processor (not shown) can combine information collected by the color channels to recover a color image.

The color channels can have fixed lenses with distinct focal lengths, or can have the same lens but distinct spacing between the lens and grating. In cameras with multiple channels of diverse focal lengths, the channel or channels presenting the sharpest focus may be used to capture high-resolution scene information, while the other, relatively defocused channels, can provide color information. Techniques to "paint on" relatively low resolution color information onto a high-resolution image are well known to those of skill in the art.

Cameras with multiple channels, whether for the same or different wavelength bands of interest, provide measures of parallax that can be combined with other information derived from orientation chirps to make a depth map of a scene. Also advantageous, information from multiple channels can be used to disambiguate depth in the case where the object exhibits deceptive structure. For example, a scene with in-focus spiral patterns may appear defocussed to a spiral ensemble. In such cases a cross check to one or more additional channels can resolve ambiguity by selecting which "reality" is most consistent with the image data provided by the disparate channels.

Some imaging applications, such as video surveillance, waste considerable power and memory resources monitoring unchanging scenes. To address this problem, some cameras support a low-power mode in which an image sensor's spatial and temporal resolutions are dramatically reduced. Fewer pixels are sensed, and less frequently, which saves power at the sensor, and the relative paucity of data saves image-processing and transmission power. Image data collected in the low-power mode is used to detect changes, and detected changes can trigger the camera to switch to a high-performance mode that supports much higher spatial and temporal resolutions.

Figure 32:
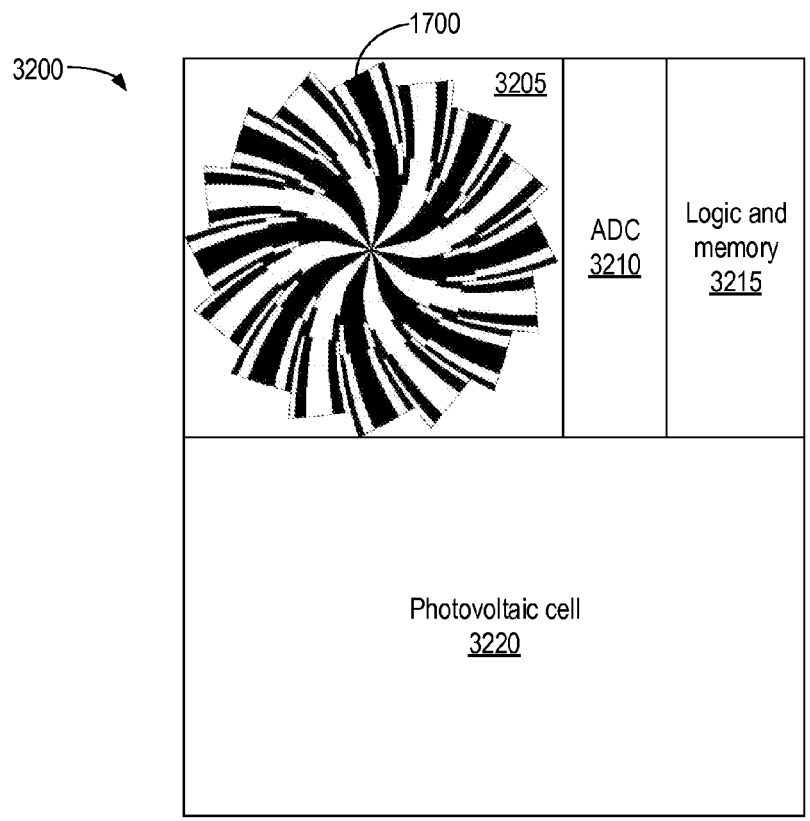
FIG. 32 depicts an image-change detector 3200 that supports a low-power mode.

FIG. 32 depicts an image-change detector 3200 that supports a low-power mode that is so efficient that it can be powered using (optionally) an integrated photocell. Detector 3200 can be instantiated on a single semiconductor die, and in this embodiment includes a photodetector array 3205 with overlying grating 1700, an analog-to-digital converter (ADC) 3210 to convert analog information from array 3205 to digital data, logic and memory 3215 to process, store, and communicate the digital signals, and a photovoltaic cell 3220 to power each of the other elements. Whether implemented on a single die or multiple die, the detector 3200 can be packaged opaquely, with a transmissive window overlying the location of the grating 1700 (and the optional photovoltaic cell).

Detector 3200 supports a low-resolution, low-power mode to sense changes in scene activity, and a high-resolution mode that captures one or more frames of higher-resolution image data responsive to detected motion. Although logic and memory 3215 can support the change detection and imaging function, some implementations may have a main function that is different from imaging, with the change detection providing an input to the chip to add situational awareness. In such cases, it may not be necessary that photodetector array 3205 contain enough elements to produce a higher-resolution image.

Figure 33:
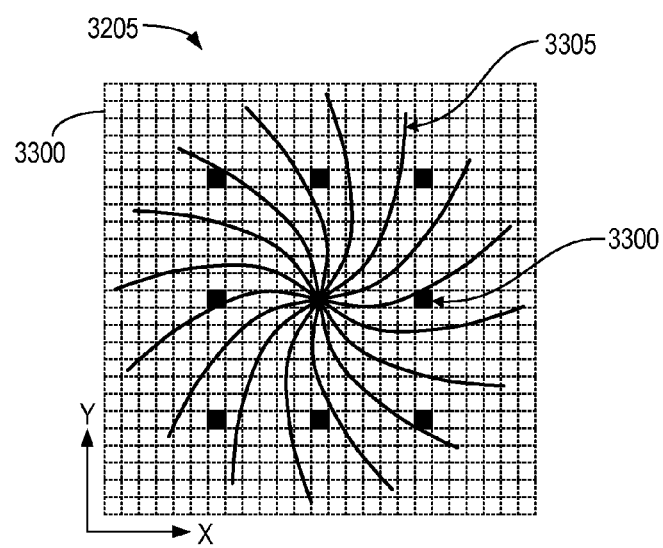
FIG. 33 depicts array 3205 of FIG. 32 as an array of pixels 3300.

FIG. 33 depicts array 3205 of FIG. 32 as an array of pixels 3300. Eight nonadjacent pixels 3300 are darkened to indicate a subset that is active in the low-power mode. An orientation chirp 3305 represents a sharply focused response from an exemplary imaged point source as it may appear at the sensor plane.

Conventional image sensors resolve a point source as a focused "dot" on a sensor array. If a camera is to detect very small movements, a rich set of active pixels much be maintained even in a low-power mode. Imagine, for example, that a point source is resolved as a sharp or blurred dot on array 3205 such that only one or a collection of neighboring pixels is illuminated. In that case, the point source could move considerably relative to the sensor without detection. At worst, the dot could move between the active pixels 3300 and off array 3205 without detection.

Chirp 3305, the result of illumination by a point source, includes "arms" of changing light intensity that illuminate many more pixels, including nonadjacent ones, than would a resolved spot, and that sweep across a great many pixels 3300 as the point source moves relative to the sensor. Consequently, fewer pixels 3300 need be polled to cover the visual field than with a system employing traditional focusing optics. In this example, movement of the point source that moves chirp 3305 a pixel or two in any direction within the X-Y plane would impact at least one of the active pixels 3300, and could thus be sensed. Sensing may involve analog-to-digital conversions of the signals from the same subset of photodiodes at different points in time. In other embodiments, analog sample-and-hold circuits and comparators can be used to signal changes in the imaged field of view. Depending upon the application, such sensed motion could be the information of interest, or could be used to bring detector 3200 out of the low-power mode to take and store one or more frames of relatively high resolution data.

Some embodiments support additional operational modes, or "stages." In one embodiment, for example, logic and memory 3215 support a three-state machine comprising a sentinel stage, a tentative stage, and a confirmation stage. In the sentinel stage, n1 pixels are monitored and if k1 (<n1) of these pixels change by a criterion value $\theta_1$ between successive image frames, then the state machine transitions to the tentative stage. In the tentative stage, n2 pixels are monitored and if k2 (<n2) of these change by a criterion value $\theta_2$ between successive frames, then the state machine transitions to state 3, otherwise the system reverts to state 1. If the system is in state 3, n3 pixels are monitored and if k3 n3) of these change by a criterion value $\theta_3$ between successive frames, then the state machine emits a signal denoting image change detected and remains in state 3, otherwise the system transitions to state 2.

One benefit of this system is that, because of the grating optics, each photodetector pixel responds to a range of positions in the field of view; thus the number of pixels that needs be monitored is lower (dissipating lower power) than in a traditional lens-based system, in which each pixel responds to a very small range of positions in the field of view. Circuit analyses show that some ADC embodiments can obtain sub-400 nW image change detection, with the power required of ADC 3210 dominating. Address generator circuits for polling subsets of pixels in support of reduced power consumption are well known to those of skill in the art, so a detailed discussion is omitted.

Photovoltaic cell 3220 provides sufficient power to support the low-power mode in ambient light, with enough extra to charge integrated or external energy-storage devices capable of supporting bursts of use in the high-performance mode. In some embodiments detector 3200 includes a separate or integrated RFID chip and associated antenna to allow image data to be retrieved wirelessly. Detector 3200 can support other forms of wired or wireless connections, as will be understood by those of skill in the art. An example of array 3205 with a grating 1700 is detailed in an accompanying document entitled "Ultra-Miniature Low-Power Lensless Image Change Detector," which is incorporated herein by reference.

Array 3205 and grating 1700 can be created using standard CMOS processes, and its formation is thus compatible with any number of functional blocks. Virtually any integrated circuit that might benefit by inclusion of an imaging device can be adapted to include one. For example, a technology referred to as "smartdust" describes systems in which many microelectromechanical systems (MEMS) can be operated on a distributed, wireless computer network to collectively perform various sensing and communication tasks. Smartdust devices can be on the order of a few millimeters on a side, which is easily sufficient to incorporate a sensor of the type detailed herein. In one embodiment, for example, the inventors created a 128×128-pixel sensor that is 200 microns on a side. Image sensors of the type detailed herein can be integrated so inexpensively that they can be incorporated into credit cards and other forms of identification for security purposes, or to facilitate vision systems in the field of microrobotics.

Figure 34:
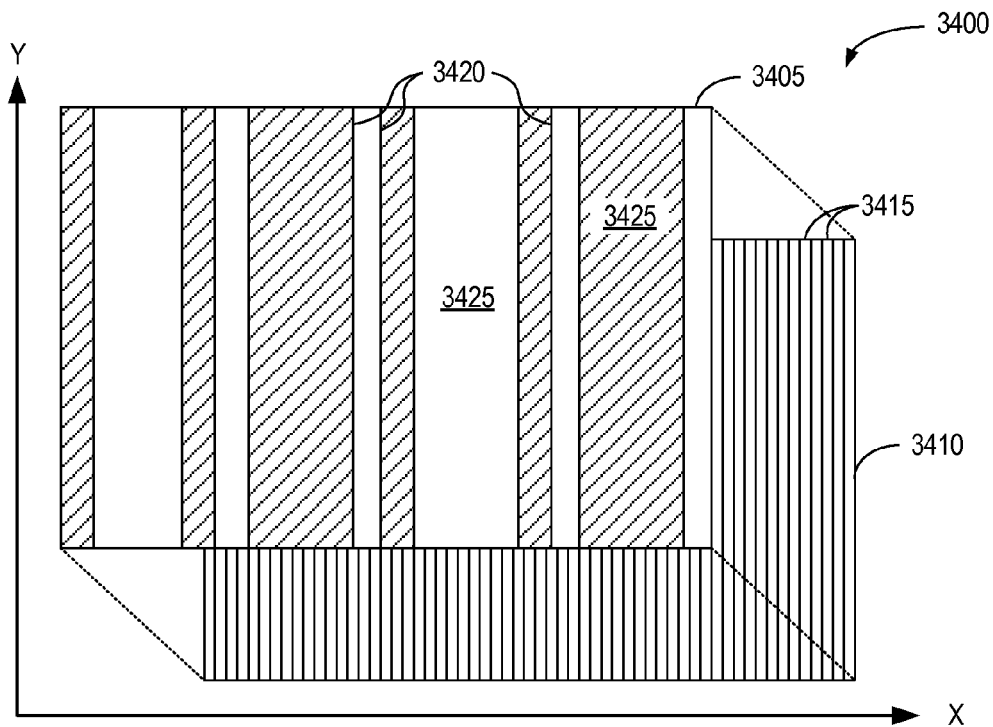
FIG. 34 depicts an image sensor 3400 with a grating 3405 overlaying or suspended above a one-dimensional array 3410 of photosensors 3415 (e.g., photodiodes).

FIG. 34 depicts an image sensor 3400 with a grating 3405 overlaying or suspended above a one-dimensional array 3410 of photosensors 3415 (e.g., photodiodes). Grating 3405 exhibits a PSR that spreads out image features to illuminate patterns across the underlying pixels. Grating 3405 has parallel odd-symmetry boundaries 3420, and may have features 3425—vertical bands—of the same or different widths, or of varying widths along one or more boundaries. In one embodiment, grating 3405 has sets of three collections of vertical bands, each band optimized for a different band of visible wavelengths (short-, medium-, and long-wavelength light, respectively). Parallel boundaries with the requisite diversity of widths and spacings to sample a sufficient number of spatial frequencies can image one-dimensional images, e.g., barcodes, or can track the relative movement of objects or gratings over a horizontal dimension X.

Sensor 3400 extracts information along a horizontal axis X. A processor (not shown) can process patterns captured by array 3410 using Ridge Regression with Tikhonov regularization and thresholding to recover the image. The aspect ratio of pixels 3415 tend to average intensity along vertical lines, which improves signal-to-noise ratios. In the case of a barcode, the resultant image can be used as input to a traditional process for the reading of barcodes, which can be performed by the processor or elsewhere.

Sensor 3400 can be adapted for infrared (IR) image detection. The materials used in the manufacture of IR lenses (e.g., monocrystalline Germanium) are generally expensive relative to that for visible light, and the cost of IR lenses tends to scale with the cube of their linear size. As a result, IR sensors are made small to reduce the cost to a practical level. The small size dictates a small thermal sensor with a high accuracy-to-size ratio. There are only a few materials and techniques able to give good room-temperature thermal performance in a pixel of the scale of thermal wavelength (about 10 μm) on a side. High-quality vacuum-sealed thermal transducers are the current industry standard because they offer adequate performance at the appropriate size. However, such transducers are prohibitively expensive. Sensor 3400 eliminates the need for a separate lens, and dramatically reduces the size and volume of IR transmissive material. Inexpensive thermal optics allow for sensors with relatively greater areas, so the thermal accuracy per unit area can be made considerably lower without overly compromising the performance. Larger, less expensive thermal transducers can therefore be used.

Figure 35:
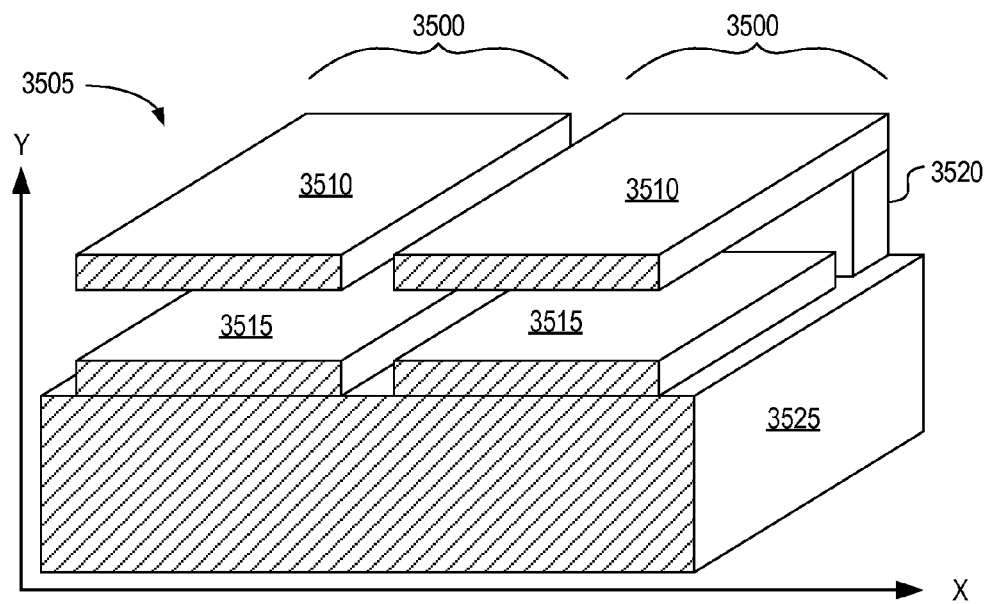
FIG. 35 is a cross-sectional view of two pixels 3500 of a 1D array 3505—a bolometer—that can be used for array 3400 of FIG. 34 in service of an IR camera.

FIG. 35 is a cross-sectional view of two pixels 3500 of a 1D array 3505—a bolometer—that can be used for array 3400 of FIG. 34 in service of an IR camera. Each pixel 3500 includes a strip of IR-absorbing material 3510 suspended over a reflector 3515 via a pair of electrical contacts 3520 (only one contact 3520 is shown). The elements are mounted on a substrate 3525 of e.g. silicon. Each strip 3510 exhibits a resistance between its respective contacts 3520 that varies with exposure to near-IR radiation. Reflectors 2515 can be included to improve sensitivity by reflecting IR light back up toward material 3510. Circuits periodically read the resistance value for each strip of material 3510 to form a one-dimensional image of the pattern to which array 3505 is exposed.

Strips 3510 are separated from one another, reflectors 3505, the overlaying grating (e.g. grating 3405 of FIG. 34), and related circuitry for thermal isolation. In some embodiments sensor 3400 is sealed and either evacuated or the air is replaced with a gas with lower thermal conductivity.

Strips 3510 are on the order of tens of microns wide. Their aspect ratio can be made high (e.g., at least 10:1). Strips with high aspect ratios tend to average intensity along their lengths, which increases signal-to-noise ratios, and suffer reduced influence from the thermal conductance of contacts 3510. Also important, the relatively low cost of gratings relative to conventional IR lenses means that both the focusing optics and the sensors can be made considerably larger and more sensitive for a given price point. Strips 3500 are thermal, as opposed to photonic, detectors, and can be e.g. thermistors, thermocouples, or resistive thermal devices; advantageously, these devices provide a spectral range of lower frequencies than photodiode or photovoltaic detectors. In some embodiments, for example, strips 3510 have a room-temperature spectral range of over five microns (e.g., between five and twenty microns). Suitable detectors can be made using micro-fabrication techniques detailed in U.S. Pat. No. 8,709,702 to Flemming et al., which is incorporated herein by reference.

Bolometer pixels are about one centimeter long in one example. Such pixels can be manufactured using a bulk process such as inkjet printing, LCD manufacturing technology, or roll-to-roll printing to reduce or minimize manufacturing costs. The pitch of pixels 3415 could be e.g. 50 μm, yielding about 200 thermal measurements per cm along the dimension perpendicular to the pixels (e.g., the X axis in FIG. 34). In other embodiments bolometer pixels are arranged in a 2D array beneath a 1D grating. In such cases image intensity can be averaged along columns of pixels perpendicular to the 1D grating for improved signal-to-noise ratios. In still other embodiments both the grating and sensor can be 2D to produce 1D or 2D images. The pixels can be of e.g. pyroelectric or ferroelectric materials in other embodiments, or can include different types of materials to produce independent measurements.

Many thermal sensing applications do not require a full thermal video—they just need to measure where a moving warm body is in a scene. For example, motion detectors are employed to e.g. turn lighting or heating on or off, or to provide intruder alerts. Unlike visible scenes where illumination changes, moving shadows, and so forth can cause large changes to the luminance of a stationary object, a stationary thermal body (at least one with high emissivity) will not change its thermal emission very quickly. Compare for instance a hand that is 10K warmer than the background moving around a scene in a 30 fps video. The thermal time derivative of the scene pixels influenced by the hand motion is up to 300K/s: much faster than any household warming process other than perhaps the onset of flaming.

Figure 36:
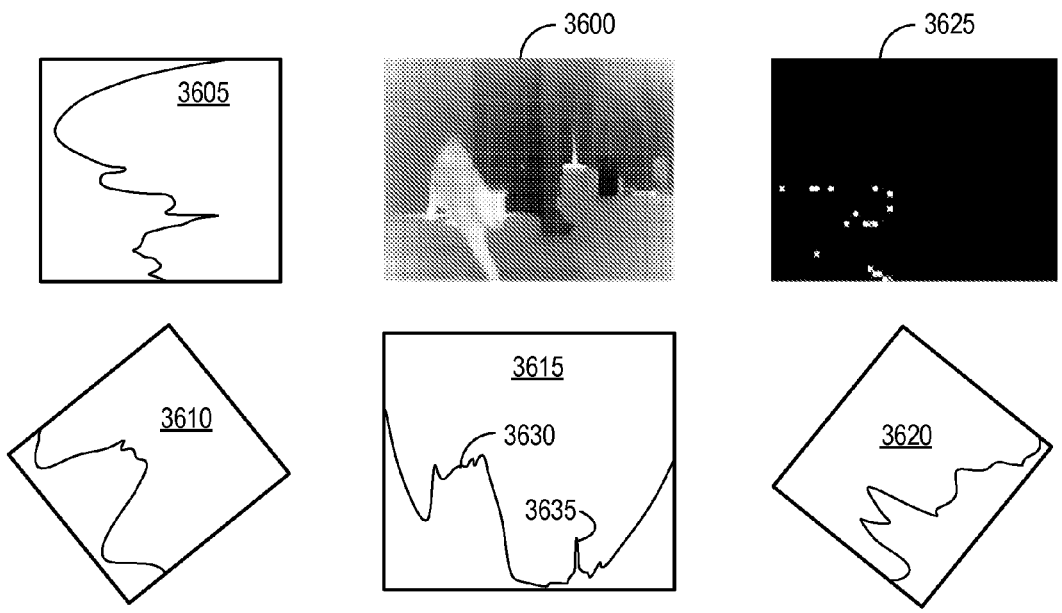
FIG. 36 illustrates how multiple 1D sensors arranged at different orientations relative to a scene can be used to locate sparse moving thermal objects.

FIG. 36 illustrates how multiple 1D sensors arranged at different orientations relative to a scene can be used to locate sparse moving thermal objects. In general, a thermal scene is sampled by a collection of N one-dimensional thermal sensors at distinct orientations (typically at orientation increments of it/N radians, but see below).

In FIG. 36, a thermal scene 3600 is measured by four one-dimensional sensors (not shown), each of which has a resolution of 1×77 pixels. Each linear array measures a 1D projection of the thermal scene. Four plots 3605, 3610, 3615, and 3620 represent these projections and the relative orientations of the respective sensors around scene. For example, plot 3605 represents the horizontally averaged intensity of scene 3600, within the IR bandwidth of interest, from the top to the bottom; and plot 3615 represents the average intensity of scene 3600 over the same band from left to right. Features 3630 and 3635 show relatively high intensity along the horizontal axis due to a relatively warm cat and candle. Plot 3610, taken using a 1D sensor oriented approximately 45 degrees relative to horizontal, does not distinguish between the cat and candle.

As thermal objects move, image artifacts from each of the sensors track the objects that generates them. Information taken from multiple 1D cameras can thus be combined to resolve the 2D image, with more sensors yielding more information and better resolution. In some embodiments the sensor or sensors can be rotated to capture data at different angles, and this data too can be used to resolve a 2D scene. In FIG. 36, the top right plot 3625 is the basis pursuit denoising solution to the question "what sparse combination of locations seems to have thermal motion?" Scene 3600 is a frame from a video in which the cat is moving, and the bright spots in plots 3635 are generally representative of that movement.

To calculate where there were thermal motion sources from only a few one-dimensional projections, we solve an underdetermined tomography problem. If the thermal scene is N×N and there are four sensors, then there are 4N measurements available with which to fit $N^2$ unknowns, and in general there is a (N−4)N-dimensional space of solutions which each fit the data perfectly. We use one or more additional constraints to choose the "correct" solution out of this subspace that fits the data.

If we expect only a few locations in the scene had their temperature changed dramatically from the last capture to the next, then we can use this sparsity to find the most likely set of thermal changes. To do this, we can solve a Basis Pursuit Denoising (BPDN) problem with $N^2$ unknowns and 4N observations. BPDN problems of this scale can be solved by the In-Crowd Algorithm detailed in P. R. Gill, A. Wang, and A. Molnar "The In-Crowd Algorithm for Fast Basis Pursuit Denoising," IEEE TRANSACTIONS ON SIGNAL PROCESSING, VOL. 59, NO. 10, OCTOBER 2011 (pp. 4595-4605), which is incorporated herein by reference. BPDN also provides for noise removal in the signal—we find that noise levels of 5% are quite acceptable and do not qualitatively impact thermal motion localization. A small, modern mobile graphics processor could perform this computation at video rates. A variant can make use of the Radon transform to further speed up the problem. Another constraint upon image reconstruction is temporal continuity. Multi-frame reconstruction, using for instance Kalman filtering in the temporal and spatial domains, generally improves estimation in such circumstances by averaging over noise.

One advantage of thermal motion localization over standard thermal imaging is that thermal sensors tend to have some degree of temporal drift to them, and thus require periodic nonuniformity correction (NUC). Since this application is sensitive to the time derivative of the signals, thermal nonuniformity is less deleterious and correcting for non-uniformities can be reduced or avoided entirely.

With enough 1D information at enough orientations, the thermal scene itself, and not just its time derivatives, can be reconstructed by the inverse Radon transform, also known as filtered back projection. Even without enough 1D information for traditional techniques (such as filtered back projection) to work, a total variation or TV-norm minimization on the underdetermined tomography problem recovers scene information with a computationally tractable algorithm. One such algorithm is detailed in S. Hashemi, S. Beheshti, P. Gill, N. Paul, and R. Cobbold "Efficient Low Dose λ-ray CT Reconstruction through Sparsity-Based MAP Modeling" (Feb. 8, 2014), which is available at http://arxiv.org/abs/1402.1801. This reference to Hashemi et al. is incorporated herein by reference. For some advanced inverse techniques to run quickly, it may be advantageous to space the angle orientations with a pseudopolar set of slopes as this spacing scheme may result in fewer reconstruction artifacts when generating a rectangular array as the final image.

A 1D imaging device of the type detailed herein can be used to range thermal sources using binocular disparity. In this case, a system with two or more 1D sensors separated by some amount in the direction of their sensitivity captures information about the depth of a thermal source based on differences between the patterns captured by the two sensors.

Figure 37:
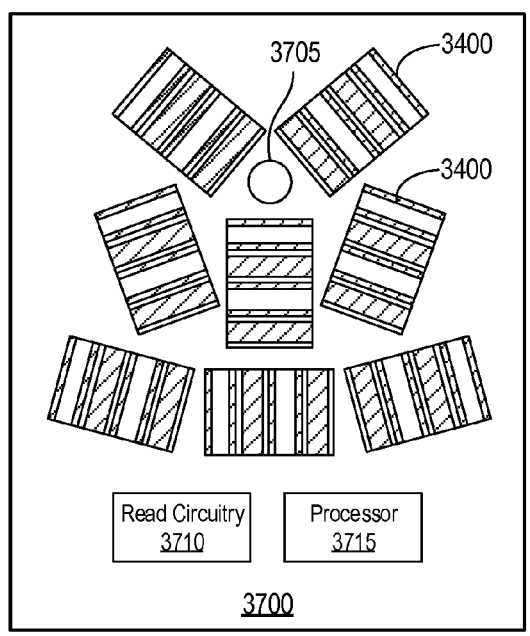
FIG. 37 depicts a camera 3700 that includes eight 1D IR sensors 3400, of the type detailed above in connection with FIGS. 34 and 35, with angular spacing of 22.5 degrees to provide independent measurements of an imaged scene.

FIG. 37 depicts a camera 3700 that includes eight 1D IR sensors 3400, of the type detailed above in connection with FIGS. 34 and 35, with angular spacing of 22.5 degrees to provide independent measurements of an imaged scene. A visible-light camera 3705 is included so that thermal changes observed by sensors 3400 can be registered with a visible-light image. Camera 3700 includes read circuitry 3710 coupled to the collection of sensors 3400 to read signals representative of their respective captured 1D images, and a processor 3715 that interprets the signals from read circuit 3710 to produce a desired output signal representative of the imaged scene.

Image sensors and the algorithms used to interpret the patterns they capture can be tailored to perform specific image-acquisition tasks. Algorithms can be simplified where they are expected to have common properties. In the case of barcodes, for example, the assumption of binary intensity can be used to simplify the process of inverting a captured pattern to recover the code. Other optical, machine-readable representations of data may have different expected properties.

Figure 38A:
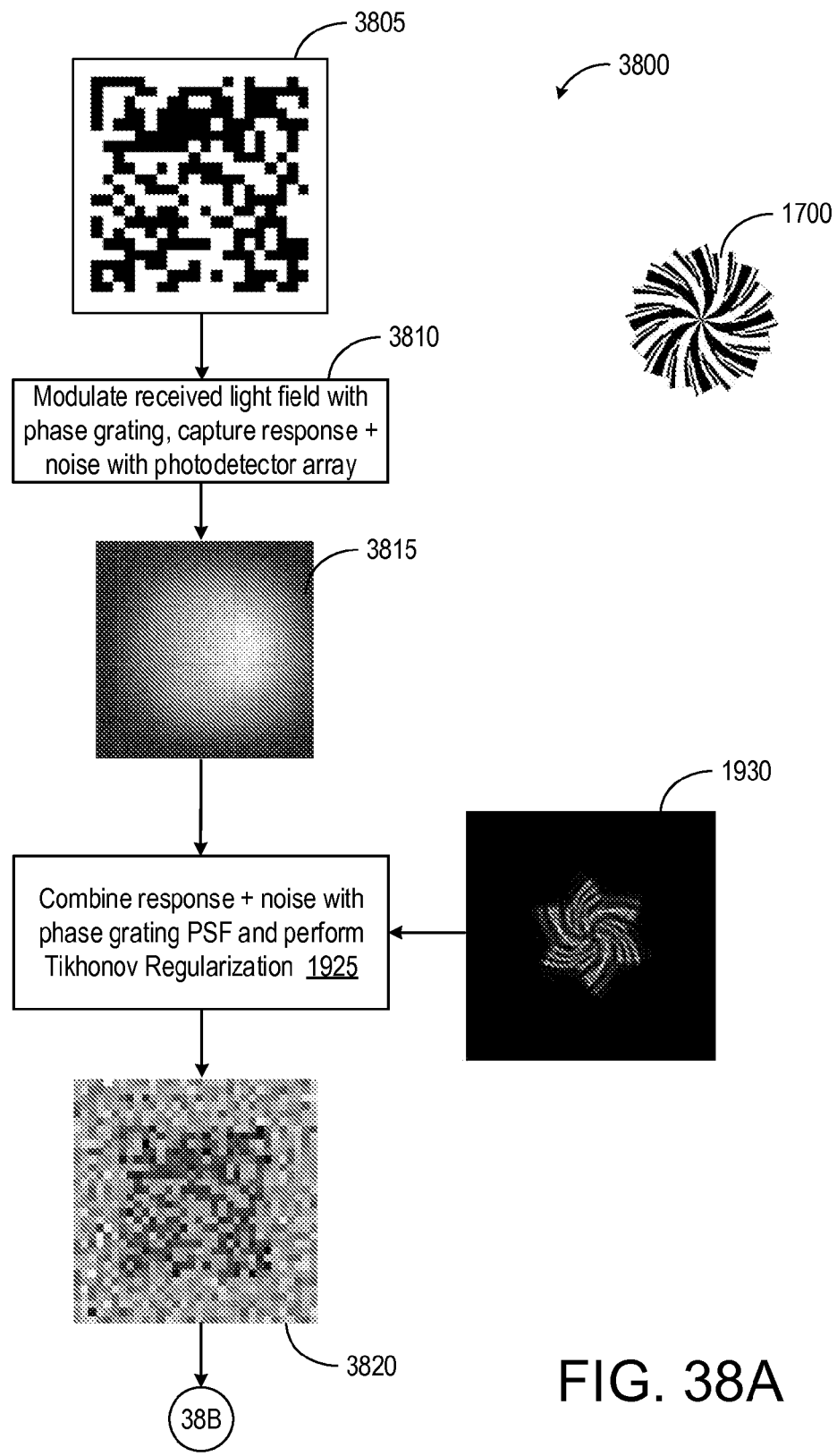
FIGS. 38A and 38B is a flowchart 3800 detailing how a QR code 3805 is captured and resolved using grating 1700 of FIG. 17 and an embodiment of an inversion algorithm that assumes a binary image.
Figure 38B:
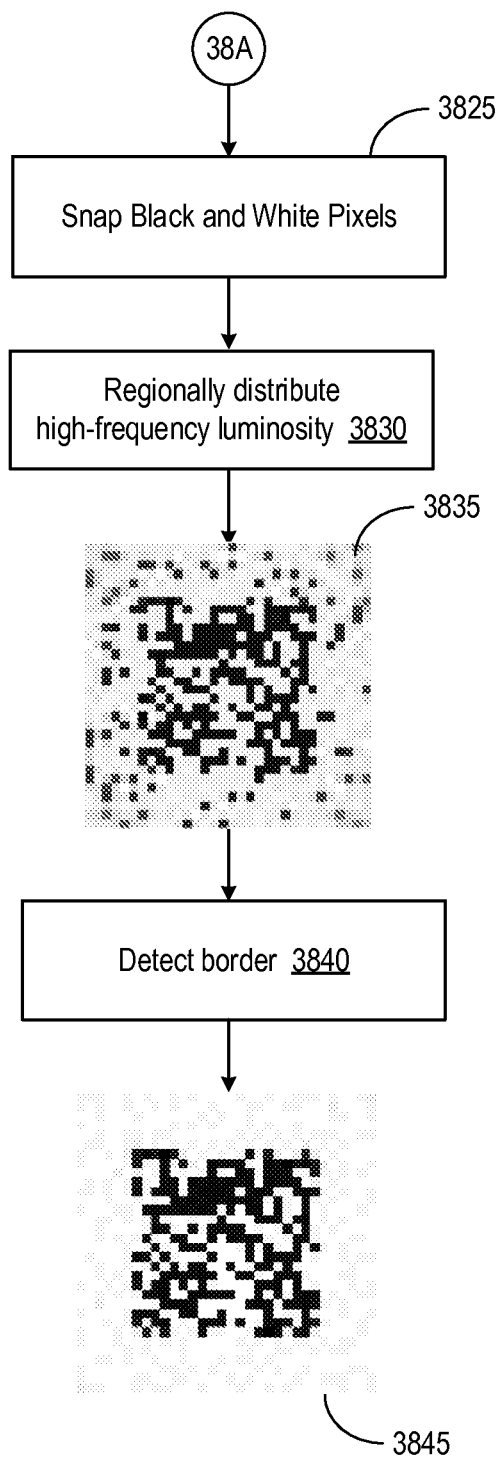

FIGS. 38A and 38B is a flowchart 3800 detailing how a QR code 3805 is captured and resolved using grating 1700 of FIG. 17 and an embodiment of an inversion algorithm that assumes a binary image. First, in step 3810, QR code 3805 is operatively positioned near an image sensor such that grating 1700 can modulate the received light field from the QR code and the underlying sensor array can capture an intensity pattern 3815 that includes both the resultant response and any noise from e.g. the sensor array. Pattern 3815 bears little resemblance to QR code 3805 but contains sufficient information, when combined with response 1930 of grating 1700, to recover the code.

Response 1930 is detailed above in connection with FIG. 19. Also noted in that discussion the response and noise represented by pattern 3815 is combined with response 1930 to form an inverse problem, which is solved (1925) to recover a noisy, grayscale version 3820 of the original QR code. This example is based on a lower-resolution calibration and increased noise relative to the example of FIG. 19 to illustrate the benefits of regularization based on e.g. the assumption of a binary image.

In general, a regularization process introduces additional information to reduce noise, solve an ill-posed problem or to prevent overfitting. To recover the original QR code in this example, the inversion process takes into account the binary property of QR codes. For example, a threshold can be applied to the data of grayscale image 3820, with the process setting pixels below and above the threshold to dark and bright, respectively (3825). Other embodiments take advantage of other known properties of the expected scene for regularization to improve image recognition.

Response 1930 can then be used to invert the resultant image. The result of that inversion is compared with pattern

3815 to determine a fit. Individual pixels of the snapped images are then inverted at random and the inversion and comparison steps repeated to determine whether the change improves or degrades the fit. These steps can be repeated until the pattern converges to a best fit. More generally, techniques such as simulated annealing and genetic algorithms can be used to find the binary-valued mark whose corresponding expected signal matches the observed data 3815 optimally. This match function can be the mean square difference, a Poisson-noise-aware metric that homoscedasticizes the data first, or, more generally, the metric can reflect expected correlations in the possible signal patterns. Then, the search for decoding the binary code becomes finding the most likely code given the observed data, from either a maximum likelihood approach (allowing any code) or a Bayesian search (where prior probabilities on the code content are factored in).

Alternatively, high and low thresholds can be used to snap bright and dark pixels of image 3820 acquired by Tikhonov regularization to known true black and white values, leaving grayscale values for pixels between the thresholds. The difference between the resultant snapped image and the Tikhonov image is due to noise. The residual luminosity "taken" from the darkened pixels and darkness taken from the brightened pixels is then redistributed among the intermediate values. Image features with low spatial frequency are generally easier to resolve than those with higher spatial frequency, so this method tends to regionally distribute high-frequency luminosity (3830). For example, a too-bright pixel means that other unknown pixels in the neighborhood are represented as too dim in the Tikhonov image. This understanding can be used to expedite convergence on the best fit. If six of eight neighboring pixels are known to be black or white, the remaining two represent the only unknowns. If the known pixels in the Tikhonov image include surplus luminosity, then the unknown pixels are likely represented as too dim.

One way to implement this redistribution therefore is as follows. First, calculate the Tikhonov reconstruction 3820 of the binary mark. Next, identify known true black and white pixels by their unambiguously dark and light values in the Tikhonov reconstruction. Next, generate a "snapped" image 3825 with the known true black and white areas having the correct values but all other values are as given by the original Tikhonov reconstruction. Next, generate the expected data that would be obtained with this snapped image. Next, compute a difference between the expected and observed data 3815. Next, apply Tikhonov-regularized image reconstruction on this difference to obtain a correction. Next, add this correction to the original Tikhonov reconstruction 3820 to obtain a lower-noise reconstruction 3835.

The resultant image 3835 resembles QR code 3805 but includes noise outside of what should be the QR code border. The process detects the border (3840) to produce the ultimate image 3845 of QR code 3805. Image 3845 is not identical to QR code 3805, but the code itself includes some error correction, and this is sufficient to correct for those errors. Image 3845 is interpreted as a QR code in a manner well understood by those of skill in the art.

Binary marks often have second-order statistics quite unlike the majority of natural scenes. For example, code 39 bar codes have only vertical orientations, and QR codes have an approximately flat power spectrum up to spatial frequencies governed by the reciprocal of the width of their constituent dots. In contrast, natural scenes typically have a $1/f^2$ power spectrum.

Since locally the operation of diffractive gratings is approximately a convolution, the power spectrum of the sensed signals on the photodiodes will be approximately the product of the Fourier amplitude spectra of the grating's PSF and the Fourier amplitude spectrum of the scene. Since the power spectra of bar codes and QR codes are unlike those of the majority of natural scenes, the power spectra of the sensor readings will likewise be conspicuously distinct when QR codes or bar codes are present. Therefore, using only a cursory sampling of some of the second-order statistics of the sensor readings, one can determine whether an object in the field of view is e.g. a bar code or a QR code. This cursory sampling could have a very low false positive rate when the sensor is presented with the vast majority of natural scenes. Computations employed to image and interpret a such codes can thus be avoided to save power and processor bandwidth.

Eyewear-based mobile displays, such as Google Glass, Samsung Galaxy Glass, and other systems need to know accurately and quickly the direction of gaze of the eye, for instance to determine the user's focus of interest, to offset visual displays and to control pointing. One method for estimating the direction of gaze in a human eye is through monitoring the position of the Purkinje images—the two-dimensional spatial locations of the images of a small source reflected from four surfaces in the eye (outer cornea, inner cornea, outer eye lens and inner eye lens). In some systems, the source is a small IR LED and the image monitor an IR lensed camera.

Purkinje image-based gaze detection can be achieved in eyewear, where an IR LED mounted on the eyewear frame (for instance) and a small imager, mounted elsewhere on the eyewear frame is used to monitor the location of the Purkinje images. Often, processing is done on a remote computer, for instance a mobile device or dedicated processor.

The space and weight requirements for the sensor are severe—especially its thickness requirement. A lensless smart sensor, with grating and processing optimized for detecting the location of Purkinje images, would support eye gaze tracking.

Ocular accommodation is the process by which the eye-lens changes its curvature (under control of the ocular ciliary muscles) for focusing on near or far objects. The location of the Purkinje images can be used to infer the curvature of the eyelens, and hence the depth of accommodation of the eye. Such information can be determined using one or more image sensors of the type described herein.

Figure 39:
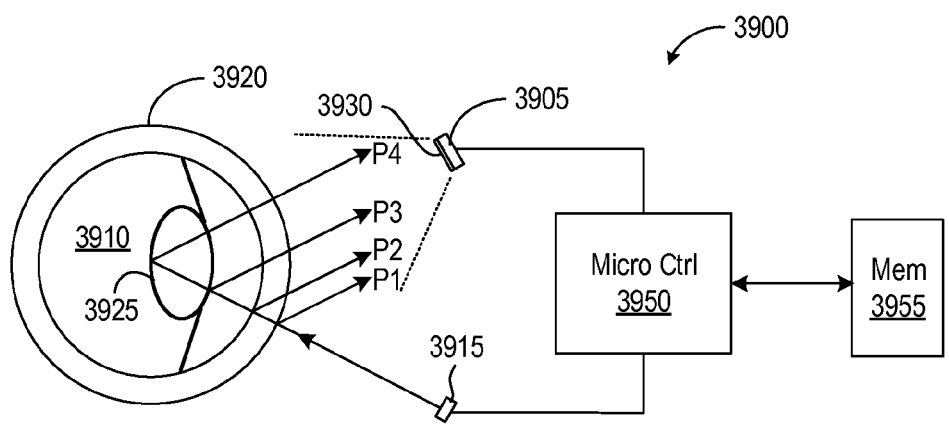
FIG. 39 depicts an eye-tracking system 3900 that employs a lenseless IR sensor 3905 to monitor the movement of an eye 3910.

FIG. 39 depicts an eye-tracking system 3900 that employs a lenseless IR sensor 3905 to monitor the movement of an eye 3910. An IR LED 3915 shines a beam of IR light into eye 3910. This light is invisible to the eye, but causes several reflections P1-P4—so-called "Purkinje images"—that can be used to track eye movement. The brightest Purkinje image P1 is reflected of the outer surface of cornea 3920, and is also called the glint; the second image P2 is reflected off the inner surface of the cornea; and the third and fourth are off the respective outer and inner surfaces of the lens 3925. Sensor 3905 can have a filter 3930 that improves the signal-to-noise ratio by excluding light outside the IR band from LED 3915. Light from LED 3915 can be modulated in some way, such as by polarization or flickered at a known rate or pattern, to aid in distinguishing the Purkinje images from the background. However the Purkinje images are recovered, the positions of those images change with eye movement. A microcontroller 3950, with access to memory 3955, can thus calculate the position of eye 3910 based on the constellation of Purkinje images.

Figure 40:
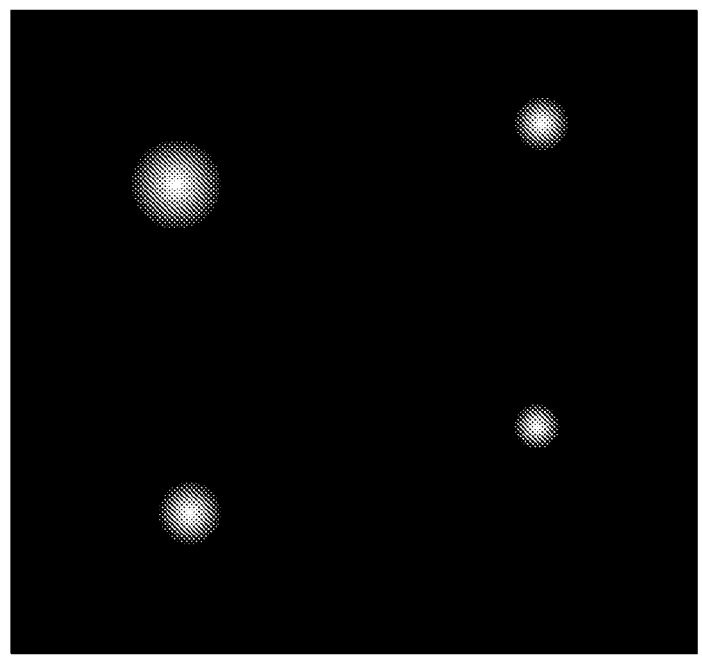
FIG. 40 depicts a simulated constellation of Purkinje images P1-P4.

FIG. 40 (prior art) depicts a simulated constellation of Purkinje images P1-P4. The span of intensities is lessened for ease of illustration; the relative intensities in an actual constellation span a range of roughly 100×.

Figure 41:
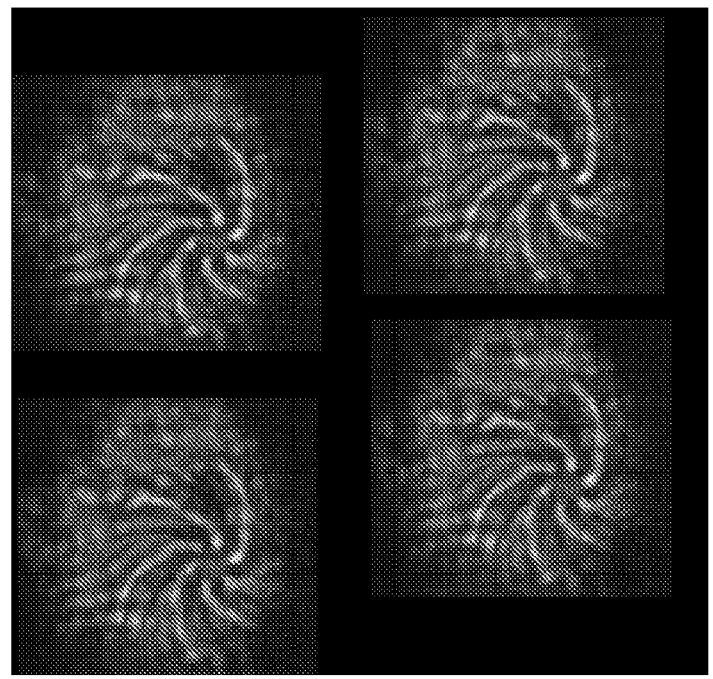
FIG. 41 represents the same constellation of FIG. 40 captured as raw photodetector sensor signals by an embodiment of IR sensor 3905 that includes a spiral grating of the type detailed in connection with FIGS. 17A and 17B, but for which the spacing of the lines of odd symmetry are optimized for the IR bandwidth of LED 3915.

FIG. 41 represents the same constellation of FIG. 40 captured as raw photodetector sensor signals by an embodiment of IR sensor 3905 that includes a spiral grating of the type detailed in connection with FIGS. 17A and 17B, but for which the spacing of the lines of odd symmetry are optimized for the IR bandwidth of LED 3915. Each Purkinje image is represented by a spiral interference pattern. These patterns can be processed, as detailed above in connection with FIG. 19, to locate the Purkinje images. The resultant data represents two dimensions for each of the four spots. Eye position and focus can be correlated with Purkinje constellations, and these correlations can be calibrated for a given eye and application. Methods for tracking eye positions using Purkinje images are well known to those of skill in the art, so a detailed discussion is omitted for brevity.

Since the task at hand is to locate the Purkinje images rather than complete imaging, several alternative grating designs could be used for this application. For instance, the radial and concentric gratings of FIGS. 9 and 10 could lead to more easily-found point locations than the spiral, and the gratings of FIGS. 15 and 16 could lead to smaller gratings than gratings that give complete spatial frequency information.

One way to locate the Purkinje images from patterns like those of FIG. 41 is to find the brightest pattern, locate the corresponding Purkinje image, and subtract the pattern from the overall sensor signal, leaving three remaining patterns. This process can be repeated for each pattern until each Purkinje image is located. As noted above, Purkinje images span a considerable range of brightness, and the brightest can saturate the sensor. The proposed method is intrinsically less susceptible to saturation since the signal from the brightest glint is spread over many, possibly hundreds, of photodetectors. However, under some circumstances several pixels on the photodetector could become saturated. In this case, with the above identify-and-subtract approach to finding the points in the image, one can take into account that several pixels may have become saturated. One might also disregard any saturated pixels in the above search. A more sophisticated method might require that any candidate set of recovered points and intensities be sufficient to saturate those pixels actually observed to be saturated.

Figure 42:
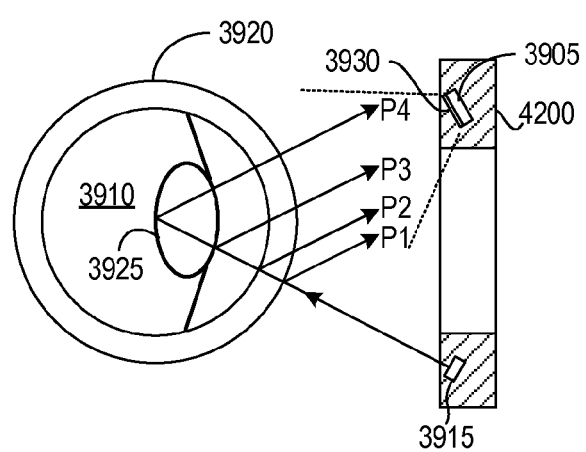
FIG. 42 depicts eye 3920 of FIG. 39 opposite a frame 4200 that supports sensor 3905 and LED 3915 in an operative position.

FIG. 42 depicts eye 3920 of FIG. 39 opposite a frame 4200 that supports sensor 3905 and LED 3915 in n operative position. Frame 4200 is e.g. a glasses frame. The remaining elements are as described above in connection with earlier figures.

Figure 43:
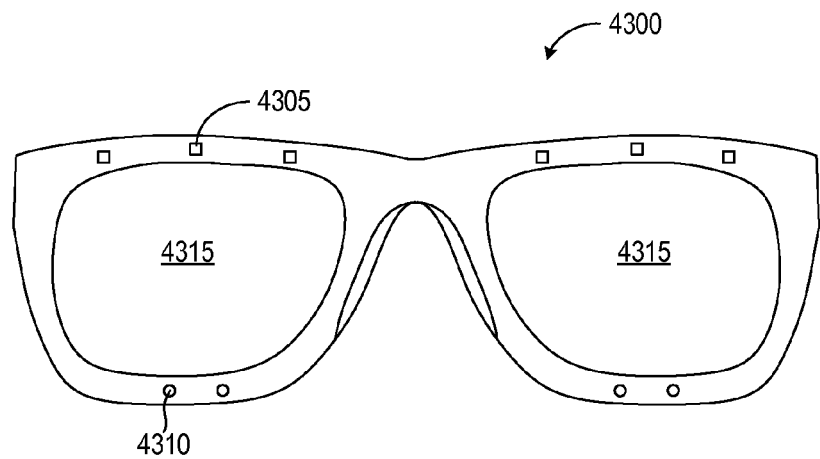
FIG. 43 depicts a glasses frame 4300 with arrays of sensors 4305 and light sources 4310 on each of two sides.

FIG. 43 depicts a glasses frame 4300 with arrays of sensors 4305 and light sources 4310 on each of two sides. Each light source 4310 produces a unique constellation of Purkinje images, and the information from sensors 4300 can be combined to improve tracking. In general, N sensors and M light sources can be provided for each eye. Sources 4310 can provide distinguishable wavelengths, polarizations, or can be time multiplexed to allow sensors 4305 to distinguish them. The lenses 4315 in frames 4300 can incorporate IR cut filters to reduce IR transmission toward the eye, and thus improve the signal-to-noise ratio for the signals that impinge upon sensors 4305.

Figure 44:
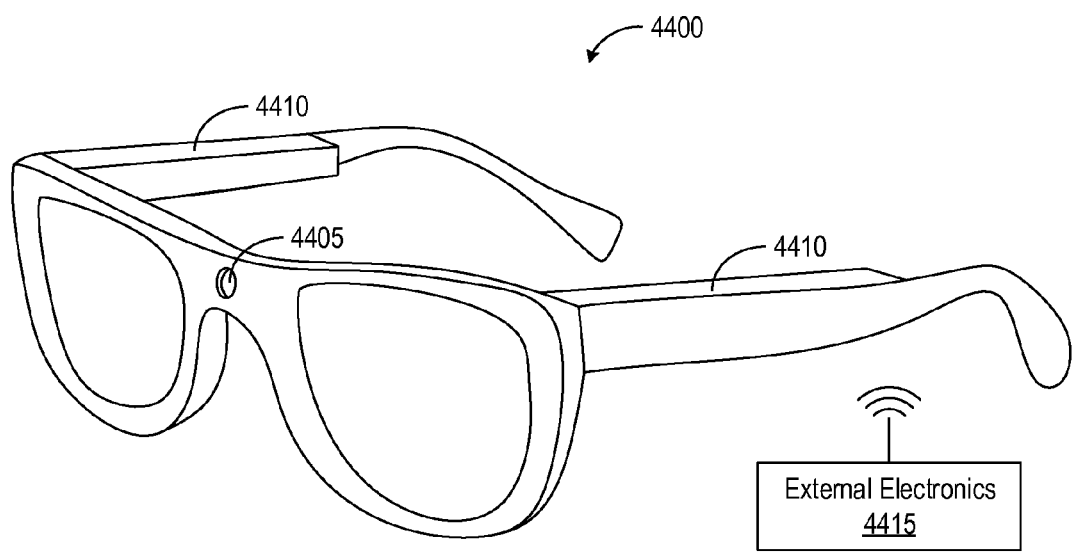
FIG. 44 depicts a pair of smart glasses 4400 in accordance with an embodiment that includes a front-facing camera 4405 in e.g. the bridge.

FIG. 44 depicts a pair of smart glasses 4400 in accordance with an embodiment that includes a front-facing camera 4405 in e.g. the bridge. The sensors and light sources are on the side opposite camera 4405, and so are not shown Some or all of the requisite electronics can be mounted on or within temples 4410. Alternatively, external electronics 4415 can be coupled to the electronics supported by glasses 4400 using either wired or wireless connections. Glasses 4400 can incorporate a heads-up display, an ear bud, or both.

Embodiments with a camera can correlate eye tracking to the image captured by the camera to record what the viewer considered. For example, glasses 4400 could detect a face and present or call out the name to the viewer, could translate a sign or menu or could report the time the viewer spent considering an advertisement or road sign.

The foregoing examples employ odd-symmetry gratings with PSFs that focus light from a point source to a spiral pattern that is spatially distributed across relatively large numbers of non-adjacent pixels. This quality is in contrast to a typical lens, in which a point source is resolved to a focused point or an unfocused blur spot. Other embodiments may incorporate different types of lenseless sensors to produce PSRs that are spatially distributed across non-adjacent pixels. For example, the gratings can produce a suitable impulse responses using Fresnel zone plates, or overlapping portions of Fresnel zone plates.

While the subject matter has been described in connection with specific embodiments, other embodiments are also envisioned. For example; while each grating detailed previously may be used in connection with photoreceptors to collect incident light, gratings in accordance with these and other embodiments can be used more generally in imaging devices that project images from photo-emitters rather than or in addition to sensing them; cameras described as using lenses could also employ other types of optical elements (e.g., mirrors); the wavelength band of interest can be broader or narrower than those of the foregoing examples, and may be discontinuous; and cameras and gratings detailed herein can be adapted for use in multi-aperture or programmable-aperture applications. Other variations will be evident to those of skill in the art. Therefore, the spirit and scope of the appended claims should not be limited to the foregoing description. Only those claims specifically reciting "means for" or "step for" should be construed in the manner required under the sixth paragraph of 35 U.S.C. § 112.

What is claimed is:

1. A system for tracking movement of an eye, the system comprising:
    an array of photoelements;
    a grating to collect light reflected from the eye, the grating having a point spread function that focuses light from a point-source to a pattern spatially distributed across non-adjacent ones of the photoelements; and
    a processor coupled to the array of photoelements to compute a location of the point source from features of the pattern.

2. The system of claim 1, wherein the grating is a diffraction grating.

3. The system of claim 2, wherein the grating comprises a zone plate.

4. The system of claim 2, wherein the pattern comprises bright lines.

5. The system of claim 4, wherein the lines form open curves.

6. The system of claim 1, further comprising a light source to direct the light to the eye.

7. The system of claim 6, wherein the light reflected from the eye comprises Purkinje spots, the processor to compute the locations of the Purkinje spots.

8. The system of claim 7, the processor to compute positions of the eye from the locations of the Purkinje spots.

9. The system of claim 1, wherein the grating is disposed over and in contact with the array.

10. The system of claim 9, wherein the grating is integrated with the array.

11. The system of claim 1, further comprising a frame to hold the grating and the array of photoelements near the eye.

12. The system of claim 11, further comprising a light source supported by the frame and positioned to direct the light to the eye.

13. The system of claim 12, wherein the light comprises infrared light of a wavelength band.

14. The system of claim 13, further comprising a filter adjacent the grating to block second light outside the wavelength band.

15. The system of claim 14, further comprising a lens, supported by the frame, to admit third light from a scene to the eye.

16. The system of claim 15, further comprising a second filter adjacent the lens to block fourth light within the wavelength band.

17. The system of claim 11, further comprising an image sensor fixed to the frame to image a scene opposite the eye.

18. The system of claim 17, the processor to correlate the movement of the eye with the scene.

19. The system of claim 11, wherein the frame supports the processor.

* * * * *